US006387844B1

United States Patent
Fujishima et al.

(10) Patent No.: US 6,387,844 B1
(45) Date of Patent: May 14, 2002

(54) TITANIUM DIOXIDE PHOTOCATALYST

(76) Inventors: Akira Fujishima, 710-5, Nakamaruko, Nakahara-ku, Kawasaki-shi, Kanagawa-ken 211; Kazuhito Hashimoto, New city hongodai D213, 2073-2, Iijima-cho, Sakae-ku, Yokohoma-shi, Kanagawa-ken 244; Tomokazu Iyoda, Bell Breeze Morinosato, 2-301, 12, Morinosato 3-chome, Atsugi-shi, Kanagawa-ken 243-01; Shigemichi Fukayama, 680, Takada, Odawara-shi, Kanagawa-ken 250-02; Tetsuo Yoshimoto, 3-4-44, Koyawata, Odawara-shi, Kanagawa-ken; Tokuyoshi Saitoh, 526-6, Kamo, Ichihara-shi, Chiba-ken, all of (JP)

( * ) Notice: Subject to any disclaimer, the term of this patent is extended or adjusted under 35 U.S.C. 154(b) by 0 days.

(21) Appl. No.: 09/042,609

(22) Filed: Mar. 17, 1998

Related U.S. Application Data

(63) Continuation-in-part of application No. 08/929,664, filed on Sep. 15, 1997, now abandoned, which is a continuation of application No. 08/666,375, filed on Aug. 14, 1996, now abandoned.

(30) Foreign Application Priority Data

Oct. 31, 1994 (JP) ............................... 6-267476
Oct. 30, 1995 (WO) ................. PCT/JP95/02214

(51) Int. Cl.$^7$ ...................... B01J 23/00; B01J 21/08; B01J 21/12; B32B 17/06; B32B 19/00

(52) U.S. Cl. ...................... 502/350; 502/349; 502/232; 502/240; 502/242; 428/428; 428/432; 428/702; 427/235.36; 427/255.391; 427/276.2; 427/430.1

(58) Field of Search ................................ 502/349, 350, 502/232, 240, 242; 428/428, 432, 702; 427/235, 36, 255, 391, 376.2, 430.1

(56) References Cited

U.S. PATENT DOCUMENTS 3,630,796 A * 12/1971 Yokazawa et al. ............ 156/17

(List continued on next page.)

FOREIGN PATENT DOCUMENTS

| EP | 0581216 | * | 2/1994 |
| JP | 06-293519 | | 10/1994 |
| JP | 07-51646 | | 2/1995 |
| JP | 08-99041 | | 4/1996 |
| JP | 9-71437 A | | 3/1997 |
| JP | 9-73879 A | | 3/1997 |
| WO | 97/10186 | * | 3/1997 |

OTHER PUBLICATIONS

Yasumori, Atsuo et al., "Preparation of TiO2 Fine Particles Supported on Silica Gel as Photocatalyst", Journal of the Ceramic Society of Japan, International Edition, vol. 102, No. 8.

Yasumori, Autso et al., "Preparation of TiO2 Fine Particles Supported on Silica Gel as Photocatalyst", Journal of the Ceramic Society of Japan, International Edition, vol. 102, No. 5. (no month/date available).*

(List continued on next page.)

Primary Examiner—Mark L. Bell
Assistant Examiner—Patricia L. Hailey
(74) Attorney, Agent, or Firm—Venable; Robert J. Frank

(57) ABSTRACT

A titanium dioxide film having at least photocatalytic activity, whose light linear transmittance corresponding to light having a wavelength of 550 nm is not less than 50 % and whose thickness is 0.1 to 5 $\mu$m or so, is formed on a transparent substrate constituted by a glass plate or the like. Preferably, a precoat film, which has optical transmissivity and is constituted by a $SiO_2$ film having a thickness of 0.02 to 0.2 $\mu$m or so, is provided between the transparent substrate and the titanium dioxide film. Thereby, excellent photocatalytic action and optical transmissivity can be obtained. Moreover, members composing various structures such as a glass window, which are especially required to have optical transparency, can be further provided with photocatalytic activities.

13 Claims, 14 Drawing Sheets

U.S. PATENT DOCUMENTS

| | | | | |
|---|---|---|---|---|
| 4,017,661 A | * | 4/1977 | Gillery | 428/412 |
| 4,485,146 A | * | 11/1984 | Mizuhashi et al. | 428/428 |
| 4,544,470 A | * | 10/1985 | Hetrick et al. | 204/248 |
| 4,892,712 A | * | 1/1990 | Robertson et al. | 422/186 |
| 5,032,241 A | * | 7/1991 | Robertson et al. | 204/157.15 |
| 5,035,784 A | | 7/1991 | Anderson et al. | |
| 5,547,823 A | * | 8/1996 | Murasawa et al. | 430/531 |
| 6,103,363 A | * | 8/2000 | Boire et al. | 428/325 |
| 6,106,955 A | * | 8/2000 | Ogawa et al. | 428/469 |

OTHER PUBLICATIONS

Takahashi, et al., "Dip coating of TiO2 Films Using a Sol Derived from Ti(O–i–Pr)4–diethanolamine–H2O–i–PrOH System". J. Mater. Sci. 23, 2259–2266 (1988—month not available).*

"Creation of comfortable environment for a new era" Photo–technology 21, '97 Densetsu Kohgyo Ten Electric Equipments Industry Show Month N/A (Translated).

* cited by examiner

FIG.3

| | TRANSPARENT SUBSTRATE | PRECOAT FILM COPOSITION | PRECOAT FILM THICKNESS (μm) | TITANIUM DIOXIDE FILM (μm) | TRANSMITTANCE (%) | DECOMPOSITION ACTIVITY (μl/min) |
|---|---|---|---|---|---|---|
| EXAMPLE | | | | | | |
| 1 | SLG | NONE | — — — | 4.8 | 70 | 10.5 |
| 2 | SLG | NONE | — — — | 0.3 | 75 | 0.15 |
| 3 | SLG | NONE | — — — | 1.5 | 69 | 2.43 |
| 4 | SLG | NONE | — — — | 2.3 | 80 | 8.10 |
| 5 | SLG | NONE | — — — | 3.2 | 75 | 9.48 |
| 6 | SLG | NONE | — — — | 4.1 | 70 | 10.8 |
| 7 | SLG | SiO2 | 0.1 | 0.1 | 85 | 1.53 |
| 8 | SLG | SiO2 | 0.1 | 0.6 | 91 | 5.87 |
| 9 | SLG | SiO2 | 0.1 | 1.7 | 86 | 13.1 |
| 10 | SLG | SiO2 | 0.1 | 2.3 | 77 | 14.5 |
| 11 | SLG | SiO2 | 0.1 | 3.0 | 74 | 15.3 |
| 12 | SLG | SiO2 | 0.1 | 4.2 | 72 | 15.6 |
| 13 | QUARTZ | NONE | — — — | 0.5 | 86 | 13.2 |
| 14 | QUARTZ | NONE | — — — | 2.3 | 60 | 14.4 |
| 15 | SLG | NONE | — — — | 4.3 | 78 | 10.9 |
| COMPARATIVE EXAMPLE | | | | | | |
| 1 | SLG | NONE | — — — | 0.05 | 90 | 0.01 OR LESS |
| 2 | SLG | NONE | — — — | 4.3 | 70 | 0.01 OR LESS |
| 3 | SLG | NONE | — — — | 0.1g/50cm | 10 OR LESS | 24.5 |

SLG: SODA LIME GLASS

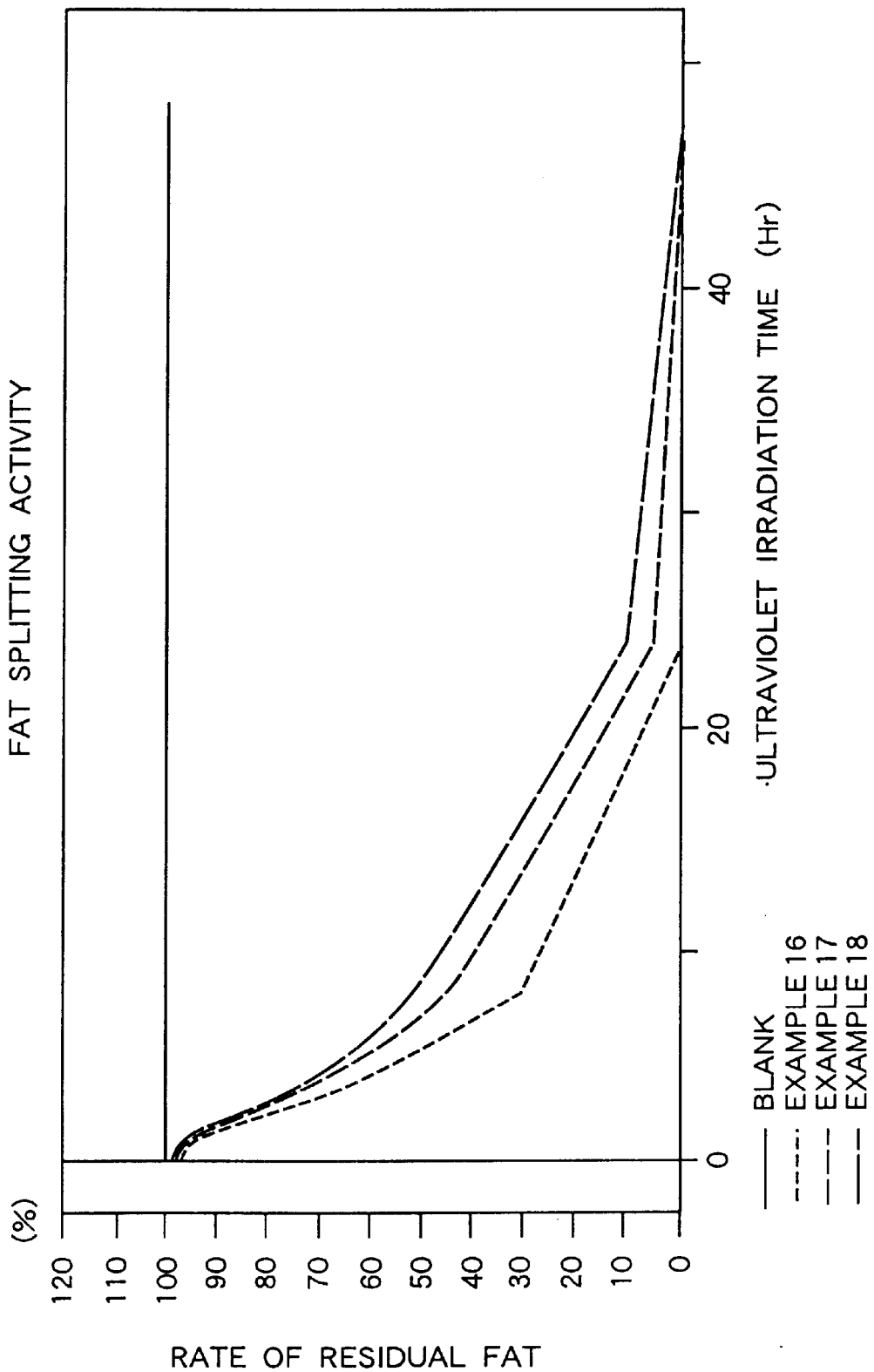

FIG.7

| | KIND OF ILLUMINATING LAMP | PRECOAT FILM COMPOSITION/ THICKNESS KIND μm | TITANIUM DIOXIDE FILM THICKNESS μm | VISIBLE LIGHT ILUMINANCE /550 lux | ULTRAVIOLET LIGHT INTENSITY/365 mW/cm | SALAD OIL SPLITTING ACTIVITY *1 |
|---|---|---|---|---|---|---|
| EXAMPLE21 | FLUORESCENT LAMP | NONE — | 4.7 | 1240 | 0.003 | 5.4 |
| EXAMPLE22 | FLUORESCENT LAMP | NONE — | 3.1 | 1290 | 0.004 | 4.7 |
| EXAMPLE23 | FLUORESCENT LAMP | NONE — | 1.7 | 1350 | 0.005 | 4.3 |
| EXAMPLE24 | FLUORESCENT LAMP | NONE — | 0.4 | 1480 | 0.007 | 0.8 |
| EXAMPLE25 | FLUORESCENT LAMP | $SiO_2$ 0.03 | 0.6 | 1470 | 0.005 | 2.3 |
| EXAMPLE26 | FLUORESCENT LAMP | $SiO_2$ 0.1 | 1.8 | 1380 | 0.005 | 6.8 |
| EXAMPLE27 | FLUORESCENT LAMP | $SiO_2$ 0.2 | 0.5 | 1460 | 0.006 | 1.7 |
| EXAMPLE28 | FLUORESCENT LAMP | $SiO_2$ 0.1 | 1.5 | 1390 | 0.005 | 5.6 |
| EXAMPLE29 | FLUORESCENT LAMP | $SiO_2$ 0.1 $ITO$ 0.2 | 1.4 | 1370 | 0.005 | 6.1 |
| EXAMPLE30 | HALOGEN LAMP | NONE — | 4.2 | 12800 | 0.007 | 10.8 |
| EXAMPLE31 | HALOGEN LAMP | NONE — | 1.2 | 13900 | 0.013 | 3.7 |
| EXAMPLE32 | HALOGEN LAMP | NONE — | 0.5 | 14200 | 0.014 | 1.7 |

*1 : μg per day·cm² IN CASE OF EXAMPLE 1 TO EXAMPLE 14 ;
μg per Hr·cm² IN CASE OF OTHER EXAMPLES

FIG.9

| | KIND OFF ILLUMINATING LAMP | PRECOAT FILM COMPOSITION/THICKNESS | TITANIUM DIOXIDE FILM THICKNESS | VISIBLE LIGHT ILUMINANCE /550 | ULTRAVIOLET LIGHT INTENSITY/365 | SALAD OIL SPLITTING ACTIVITY |
|---|---|---|---|---|---|---|
| EXAMPLE 33 | HALOGEN LAMP | μm SiO₂ 0.05 | μm 1.2 | lux 14000 | mW/cm 0.012 | 3.9 |
| EXAMPLE 34 | HALOGEN LAMP | SiO₂ 0.1 | 4.2 | 13200 | 0.005 | 11.0 |
| EXAMPLE 35 | HALOGEN LAMP | NONE | 0.8 | 55 | 0.47 | 8.7 |
| EXAMPLE 36 | HALOGEN LAMP | SiO₂ 0.1 | 0.5 | 58 | 0.64 | 5.4 |
| EXAMPLE 37 | HALOGEN LAMP | SiO₂ 0.1 | 1.2 | 52 | 0.30 | 12.2 |
| EXAMPLE 38 | HALOGEN LAMP | SiO₂ 0.2 | 0.4 | 58 | 0.64 | 5.5 |
| EXAMPLE 39 | HALOGEN LAMP | SiO₂ 0.2 | 1.0 | 50 | 0.32 | 11.8 ※2 |
| COMPARATIVE EXAMPLE 4 | FLUORESCENT LAMP | NONE | 0.05 | 1510 | 0.030 | 0.3 OR LESS |
| COMPARATIVE EXAMPLE 5 | FLUORESCENT LAMP | NONE | 4.3 | 1090 | 0.018 | 0.3 OR LESS |
| COMPARATIVE EXAMPLE 6 | FLUORESCENT LAMP | SiO₂ 0.01 | 0.1 | 1480 | 0.028 | 0.3 OR LESS |
| COMPARATIVE EXAMPLE 7 | FLUORESCENT LAMP | — | — | 1520 | 0.036 | 0.3 OR LESS |
| COMPARATIVE EXAMPLE 8 | HALOGEN LAMP | — | — | 15200 | 0.073 | 0.3 OR LESS |
| COMPARATIVE EXAMPLE 9 | BLACK LIGHT | — | — | 61 | 1.35 | 0.3 OR LESS |

*2 : μg per day·cm² IN CASE OF COMPARATIVE EXAMPLES ;

FIG.15

| | GLASS COMPOSITION | PRECOAT FILM COMPOSITION THICKNESS KIND μm | TITANIUM DIOXIDE FILM THICKNESS μm | VISIBLE LIGHT TRANSMITTANCE % | ULTRAVIOLET LIGHT TRANSMITTANCE % | SALAD OIL SPLITTING ACTIVITY *1 |
|---|---|---|---|---|---|---|
| EXAMPLE 41 | SLG | NONE — | 4.7 | 75 | 10 | 12.5 |
| EXAMPLE 42 | SLG | NONE — | 3.3 | 82 | 12 | 10.8 |
| EXAMPLE 43 | SLG | NONE — | 1.8 | 86 | 13 | 9.6 |
| EXAMPLE 44 | SLG | NONE — | 0.3 | 91 | 16 | 5.4 |
| EXAMPLE 45 | SLG | $SiO_2$ 0.03 | 0.3 | 90 | 14 | 8.4 |
| EXAMPLE 46 | SLG | $SiO_2$ 0.1 | 1.6 | 89 | 12 | 11.2 |
| EXAMPLE 47 | SLG | $SiO_2$ 0.1 | 3.0 | 83 | 10 | 12.4 |
| EXAMPLE 48 | SLG | $SiO_2$ 0.1 | 1.5 | 80 | 8 | 13.0 |
| EXAMPLE 49 | SLG | $SiO_2$ 0.1 ITO 0.2 | 1.4 | 84 | 12 | 10.9 |
| COMPARATIVE EXAMPLE 10 | SLG | NONE — | 0.05 | 95 | 35 | 0.4 |
| COMPARATIVE EXAMPLE 11 | SLG | $SiO_2$ 0.1 | 3.8 | 69 | 28 | 0.3 OR LES |
| COMPARATIVE EXAMPLE 12 | SLG | $SiO_2$ 0.1 | 5.5 | 61 *2 | 7 | 12.7 |

*1: IN $\mu g/Hr \cdot cm^2$  *2: TEST PIECE WAS CLOUED
SLG : SODA LIME GLASS

TITANIUM DIOXIDE PHOTOCATALYST

This application is a continuation-in-part of U.S. patent application Ser. No. 08/929,664, filed on Sep. 15, 1997, now abandoned, which is a continuation of U.S. patent application Ser. No. 08/666,375, filed on Aug. 14, 1996, now abandoned.

TECHNICAL FIELD

The present invention relates to a titanium dioxide photocatalyst structure that has excellent photocatalytic actions and light transmissivity (or transmittance) and enables members of various substances, which require transparency particularly, to have photocatalytic actions. The present invention further relates to a lighting device and a window glass which employ such a titanium dioxide photocatalyst structure.

BACKGROUND ART

Heretofore, there have been known photocatalysts that exhibit activities, by which the decomposition and oxidation of substances are accelerated, when irradiated with light. Recently, attempts or the like have been made to remove air pollutants such as sulfur oxides and nitrogen oxides by utilizing the photocatalysts. Moreover, attempts have been further made to use titanium dioxides as the photocatalysts (see, for example, Japanese Patent Laid-Open Nos. 6-385/1994, 6-49677/1994 and 6-39285/1994 Official Gazettes).

By the way, in recent years, there has been a growing interest in globally environmental pollution. Meanwhile, the demand for removing substances such as $CO_2$, $NO_X$ and $SO_X$ has grown. Moreover, a plan for creating amenity space by eliminating toxic substances has been devised. Thus, the demands for deodorizing living space and for making the living space antibacterial, soil-resistant and mildew-proof have grown increasingly.

It is accordingly conceived that the aforementioned titanium dioxide photocatalyst is utilized for removing such pollutants. However, in the case of the conventional titanium dioxide photocatalysts, generally, gaseous or liquid materials to be treated are introduced into a container accommodating the photocatalyst and are thus made to be in contact with the photocatalyst, and simultaneously, light is introduced from the exterior thereto and is applied onto the photocatalyst.

Further, in such a case, for the purpose of increasing the contact area between the material to be treated and the photocatalyst and efficiently applying the light onto the photocatalyst, attempts or the like have been made to produce the photocatalyst in minute-particle form or to hold the photocatalyst on a transparent base material.

However, in the case of the aforementioned conventional titanium dioxide photocatalyst, although the contact area between the photocatalyst and the material to be treated can be increased by, for instance, producing the photocatalyst in minute-particle form, the effective area of the photocatalyst, by which light is received, cannot be increased very much. Consequently, it is difficult to largely enhance the total catalysis effects thereof.

Further, in the case where the titanium dioxide photocatalyst is formed in film form on, for example, a glass substrate or the like, the titanium dioxide photocatalyst itself has low transparency. This is because it has been heretofore considered that methods suitable for forming a photocatalyst in film form to thereby obtain practical photocatalysis are limited to a method of forming a titanium dioxide sol on the substrate by sintering and a method of producing titanium dioxide in fine powder form, dissolving the powder by using a binder and then applying the dissolved powder onto the substrate. However, in the case of employing the former method, a photocatalyst, which has high activity and a certain measure of transparency, can be obtained, though it is necessary for obtaining the film, whose strength is sufficient for practical use, to set a sintering temperature at a value which is not lower than the softening temperature of glass. Thus, at least, it is impossible to form the photocatalyst on the glass substrate. Besides, regarding the light transmissivity, this photocatalyst tends to become clouded. It is difficult for this photocatalyst to transmit visible light to such an extent that the transparency can be obtained. In this sense, this photocatalyst is close to opaque. In contrast, in the case of the latter method, although the step of sintering is unnecessary, the photocatalyst becomes clouded and opaque because fine titanium dioxide powder is applied to the substrate.

Further, in the case of titanium dioxide produced in film form by performing a sol-gel method and CVD method which have been well known in the field of such a kind heretofore, the transparency can be ensured, whereas the activity of the catalyst, which has a practical level, is not obtained.

Thus, all of the conventional titanium dioxide photocatalysts, which exhibit the photocatalytic activities of practical levels, are substantially opaque. Therefore, even in the case that this conventional photocatalyst is formed on, for example, the front surface of a transparent glass substrate or the like, light applied from the back surface of the glass substrate cannot effectively reach the front surface portion of the photocatalyst. Consequently, only light applied from the front surface portion, on which the photocatalyst is formed, of the substrate can be utilized. Hence, in the case that the cleaning of indoor air is performed by forming this photocatalyst on, for instance, the surface of a window pane, it naturally follows that the photocatalyst is formed on the surface of the glass, which faces the inside of a room. Thus, only light applied from the inside of the room that can be utilized for obtaining the photocatalytic activity. Consequently, there has been a serious defect that sunlight cannot be utilized therefor.

Thus, in the case of the conventional titanium dioxide photocatalyst, titanium dioxide, which performs the photocatalysts, itself is substantially opaque. Consequently, there occurs a limit to the enhancement of the photocatalytic activity. Moreover, the range of application of the photocatalyst is extremely limited.

Furthermore, there has been made an attempt to apply powdered photocatalyst to the outer surface of a discharge lamp to thereby impart a deodorization function thereto (see Japanese Patent Laid-Open No.1-169866 Official Gazette). Additionally, there has been made another attempt to cover the periphery of an illuminating lamp with a net constituted by a glass filter, which is coated with a photocatalyst (see Japanese Patent Laid-Open No.1-139139 Official Gazette), thereby performing a deodorization by utilizing a photocatalytic action at a place where illuminance is high, namely, at a place closer to the illuminating lamp. Besides, there has been made still another attempt to decompose ambient offensive odor (or malodor) substances by depositing a titanium dioxide film on the surfaces of spectacle lenses according to a sputtering method (see Japanese Patent Laid-Open No.2-223909 Official Gazette).

However, the discharge lamp described in the aforementioned Japanese Patent Laid-Open No.1-169866 Official Gazette is configured only by applying anatase-type titanium dioxide powder, whose grain diameter is 500 Å, onto the outer surface of a discharge container. Thus, this discharge lamp is inferior to other lamps in light transmissivity and abrasion resistance. It is obvious that, even if the applied titanium dioxide is baked, a high temperature is needed and there are obtained only discharge lamps which are inferior to other lamps in light transmissivity. Therefore, in the case of this discharge lamp, the photocatalyst has little effect. Further, this discharge lamp is in a state in which the powder adheres to the surface thereof and the degree of the unevenness of the surface thereof is high. With such a structure, this discharge lamp is easily stained and is liable to gather dusts.

Moreover, regarding the air-cleaning spectacle described in the Japanese Patent Laid-Open No. 2-223909 Official Gazette, although the titanium dioxide films are formed on the surfaces of the spectacle lenses by a physical method such as an ion plating method, the objective device configuration and data concerning the identification of titanium dioxide, the crystalline structure of the (thin) films and the judgement on the deodorization effects are not sufficiently disclosed in this official gazette.

Furthermore, in the case that the films are formed by the physical method such as a sputtering method, a considerably long film formation time is required to obtain a film thickness by which practical photocatalytic actions can be caused. This causes problems in respect of the productivity and the stability of the quality of films. Consequently, such physical film formation processes have drawbacks in that such processes are difficult to be used as manufacturing processes of general-purpose industrial products.

Further, the conventional illuminating lamp coated with a titanium dioxide film (or layer) has defects in that the light transmissivity is low because the powdered titanium dioxide film is used and thus this film is substantially opaque, in that it is difficult for light, which is emitted from the inside of the illuminating lamp, to reach the outermost surface of the titanium dioxide layer, to which contaminants in the air most easily adhere, in that therefore, the quantity of available light is considerably smaller than the quantity of available light in the case of depositing a transparent titanium dioxide film on the lamp, in that thus, the amount of decomposed contaminants is very smaller in comparison with the amount thereof in the latter case, and in that the surface of the lamp is easily stained owing to the unevenness of the surface thereof.

Incidentally, in the case of the discharge lamp and the spectacle, which are respectively described in the aforementioned Japanese Patent Laid-Open Nos. 1-169866 and 2-223909 Official Gazettes, objects to be decomposed are mainly offensive odor substances. Namely, primary objects or purposes of these discharge lamp and spectacle are not the decomposition of fat and oil.

The present invention is accomplished against the aforementioned background. The present invention aims at providing a titanium dioxide photocatalyst structure that has excellent photocatalytic actions and light transmissivity and enables members of various substances, which require transparency particularly, to have photocatalytic actions and further aims at providing a method for producing such a photocatalyst structure.

SUMMARY OF THE INVENTION

To solve the aforesaid problem, in accordance with the present invention, there is provided a titanium dioxide photocatalyst structure which comprises:

a transparent glass substrate having first and second opposing surfaces, the first surface of the aforesaid substrate receiving light from an external light source; and a titanium dioxide film having first and second opposing surfaces, a light transmittance of the aforesaid titanium dioxide film being at least 50% for light having a wavelength of 550 nm, the first surface of the aforesaid titanium dioxide film being formed on the second surface of the aforesaid substrate, whereby light transmitted from the aforesaid external source through the first and second opposing surface of the aforesaid substrate and through the first surface of the aforesaid titanium dioxide film to t he second surface thereof causes photocatalytic action to be generated on the second surface of the aforesaid titanium dioxide filming.

Further, in accordance with another aspect of the present invention, there is provided an illuminating device having a light emitting portion, provided in a glass container, for radiating light, which includes visible light as a main component and further includes an ultraviolet component, which comprises: a titanium dioxide film which is formed on a surface of the aforesaid glass container having first and second opposing surfaces and is adapted to have a photocatalytic activity due to absorption of ultraviolet light and to transmit at least 50% of visible light, whose center wavelength is 550 nm, radiated from the aforesaid light emitting portion and having passed through the aforesaid glass.

Moreover, in accordance with another aspect of the present invention, there is provided a window glass provided with a titanium dioxide film, formed on at least one of sides of a glass sheet or plate, wherein the aforesaid titanium dioxide film is adapted to have a linear transmittance of 50% or more when measured by using light having a wavelength of 550 nm and to have a linear transmittance of 50% or less when measured by using light having a wavelength of 350 nm, and wherein the aforesaid titanium dioxide film has ability to decompose 0.5 $\mu$g of linoleic (or linolic) acid per square centimeter of the film for one hour in a case that the film is irradiated with ultraviolet light including light, whose wavelength ranges from 300 to 400 nm, and having a power density of 5 mW/cm$^2$.

Thus, a titanium dioxide film, which has at least photocatalytic activity and light transmittance corresponding to light having a wavelength of 550 nm is not less than 50%, is formed on a transparent substrate. Thereby, the titanium dioxide photocatalyst structure can have excellent photocatalytic action and optical transmissivity. Moreover, the titanium dioxide photocatalyst structures can be used as members composing various structures such as a glass window, which are especially required to have light transmissivity.

This is owing to the fact that as a result of setting the titanium dioxide film in such a manner that the light transmittance corresponding to light having the wavelength of 550 nm is not less than 50%, the substantially increasing of light irradiation efficiency required to obtain photocatalytic activities can be easily achieved and simultaneously, the transparency corresponding to visible light can be ensured. Namely, if setting the titanium dioxide film in such a manner that the light transmittance corresponding to light having the wavelength of 550 nm is not less than 50%, the titanium dioxide film inevitably has the transmissivity corresponding to light, which gives the photocatalytic activity (and which has the wavelength of about 400 nm), in such a way that the degree of the transmissivity is sufficient to effectively utilize light applied thereto from the front and back thereof. Therefore, when both of the front and back surfaces of this titanium dioxide photocatalyst structure are irradiated with different light, respectively, the light rays respectively coming from both of the surfaces thereof reach the surface portion, which is in contact with the exterior, of the titanium dioxide film in such a manner as to be added to each other. Namely, the efficiency in applying light onto the surface portion of the titanium dioxide film can be substantially increased. Thereby, the photocatalytic activity of the surface portion of the titanium dioxide film can be substantially increased in response to this, so that excellent photocatalytic activity can be obtained. Simultaneously, as a consequence of setting the titanium dioxide film in such a manner that the light transmittance corresponding to light having the wavelength of 550 nm is not less than 50%, the sufficient transparency corresponding to visible light can be secured inevitably. Consequently, this titanium dioxide photocatalyst structure can be used as a member of various structures especially required to have the transparency, for example, a glass window, an illuminating system, a mirror and a glass door. The present invention can have distinguished advantages in that actions of eliminating carbon dioxide and air pollutants (for example, $NO_X$ and $SO_X$) from indoor space, of deodorizing the indoor space and of making the indoor space antibacterial, soil-resistant and mildew-proof are achieved by the window pane itself without using special equipment. Additionally, the present invention can obtain eminent merits in that in the case of cleaning the room by applying the photocatalyst structure to the window pane, sunlight can be extremely utilized. Moreover, especially, in the case of applying the photocatalyst structure of the present invention to a building or the like, in which glass materials are highly used, of the type that has become common in recent years, the photocatalyst structure of the present invention has immeasurable advantages in cleaning the living space. In addition, the photocatalyst structure of the present invention can be applied to a glass door or the like of a shelf, which includes the door or the like, for storing, for instance, precision devices such as a camera which should be kept away from molds and corrosion. Thus, the range of application of the photocatalyst structure of the present invention is extremely wide. Further, a titanium dioxide film having sufficient photocatalytic activity and simultaneously having the light transmittance, which is not less than 50% correspondingly to light having a wavelength of 550 nm, can be obtained by setting the thickness of the titanium dioxide film at a value of 0.1 to 5 $\mu$m. In the case that the thickness of the photocatalyst structure is less than 0.1 $\mu$m, sufficient photocatalytic activity cannot be obtained. In contrast, in the case that the thickness of the photocatalyst structure exceeds 5 $\mu$m, the light transmittance corresponding to the light having the wavelength of 550 nm is less than 50%. Consequently, sufficient transparency cannot be obtained.

Moreover, the titanium dioxide film contains anatase crystals. Thereby, the photocatalyst structure further excels in photocatalytic activity.

Furthermore, a precoat film having transparency is disposed between the transparent substrate and the titanium dioxide film. Thus, the material of the transparent substrate penetrates into the titanium dioxide film, so that the photocatalytic activity of the titanium film can be prevented from being degraded. Moreover, the range of materials of the transparent substrate to choose can be extended. Furthermore, in the case of forming a titanium dioxide film directly on the transparent substrate, the titanium dioxide film should have a thickness sufficient to the extent that even when the material of the transparent substrate penetrates into the titanium dioxide film, the material cannot reach titanium dioxide on which charge separation action should be exerted. The present invention, however, eliminates the necessity of making the film thick to such an extent. Thus, even when the titanium dioxide film is made to be extremely thin regardless of what kind of materials the substrate employs, the photocatalytic activity can be sufficiently enhanced. This is very significant from the view point of essential enhancement of efficiency in irradiating light, and of improvement of transparency.

In the case that the thickness of the precoat film is 0.02 to 0.2 $\mu$m, even when taking materials, which can be employed as those of the precoat film, into consideration, the photocatalyst structure of the present invention can obtain advantages in that sufficient transparency can be ensured and that the penetration of the material of the substrate can be blocked. Conversely, in the case that the thickness of the precoat film is less than 0.02 $\mu$m, it is difficult to have a sufficient effect on the blockage of the penetration of the material. Further, even in the case that the film, whose thickness exceeds 0.2 $\mu$m, is formed, the photocatalyst structure cannot have further advantageous effects on the blockage of the penetration of the material. Moreover, an operation of forming the film becomes complicated. Furthermore, if the film is made of some material, the sufficient transparency cannot be ensured.

In the case that glass is used as the transparent substrate, the extremely wide range of application of the photocatalyst structure of the present invention can be achieved, as previously described. In this case, if the precoat film is made of $SiO_2$, the best transparency and the highest effects on the blockage of penetration of the materials of the substance can be secured.

In a glass container, a titanium dioxide film, which has photocatalytic activity due to ultraviolet light absorption and is, on the other hand, adapted to transmit a light component that is radiated from the aforementioned light emitting portion and is then transmitted by the aforesaid glass container, with the intention of irradiating the photocatalyst, is formed on the surface of the glass container. Thickness of this titanium dioxide film is set in such a manner as not to be less than a value, which is necessary for having photocatalytic activity whose degree is equal to or higher than that of photocatalytic activity required to decompose and remove fat and oil ingredients deposited on the surface of this film in an ordinary life space, and in such a manner as not to be more than a value at which the aforementioned light component, whose magnitude is equal to or more than a magnitude necessary for attaining the object of irradiating the photocatalyst, is transmitted by the film. Thus, there can be obtained an illuminating lamp that has a self-cleaning function in addition to securing the illuminating function.

Moreover, a titanium dioxide film, which has photocatalytic activity due to ultraviolet light absorption and is, on the other hand, adapted to transmit 50% or more of visible light that is radiated from the aforementioned light emitting portion and is then transmitted by the aforesaid glass container and has wavelengths in a range whose center wavelength is 550 nm, is formed on the surface of the glass container. Thus, there is obtained an illuminating lamp that has an extremely excellent self-cleaning function of efficiently decomposing fat and oil gradients typified by oil stains and tobacco tars, which are deposited on the surface thereof, by light emitted from the illuminating lamp itself. This titanium dioxide film of the present invention, which is excellent in the photocatalytic actions, has not only the fat-and-oil decomposing function but has an antibacterial function and a deodorization function. Thus, for example, lamp blacks and tobacco tars deposited on the surface of an interior lamp are relatively easily decomposed by light emitted by the illuminating lamp such as a fluorescent lamp itself. It is, thus, easily conjectured that, as a result, this illuminating lamp is dust-proof and dirt-resistant and excels in an anti-fouling function. Furthermore, this illuminating lamp further has an advantage in that minute quantities of malodorous substances contained in an interior space or unwanted bacteria floating in an accommodation space are easily decomposed or annihilated when adhering to the surface of the glass container or tube of the illuminating lamp. Therefore, this illuminating lamp can be put to various uses such as illumination of: facilities which are required to be kept clean and to accommodate many people gathering therein, especially, hospitals, clinics, medical offices, old-age homes, long-term sanatoria, hotels, offices and food factories; the inside of transportation means such as a train and a bus; and of tunnels and roads.

Incidentally, the provision of the titanium dioxide film on the surface of a glass container has other advantages in that sufficient photocatalytic actions are obtained by utilizing relatively intense light irradiated on the surface of the glass container, and that radiation of harmful ultraviolet light to the exterior is prevented by being almost completely absorbed and being thus cut off by this titanium dioxide film on the surface of the glass container. Further, hitherto, in the case of a fluorescent lamp, it is usual that an ultraviolet absorbent is added to a phosphor (or fluorescent substance) to be applied onto the glass container. The provision of the titanium dioxide film can eliminate the necessity of such a step. In this case, the magnitude of ultraviolet light reaching the titanium dioxide film provided on the outer surface of the fluorescent lamp container is further increased, so that the function of splitting fats and oils is further enhanced.

Furthermore, in the case of a halogen lamp, the fat-and-oil splitting activity is very high. Thus, the halogen lamp is suited to use at places in an ordinary environment in which the lamp is used, especially in an environment where the lamp is very liable to be stained, for instance, in the vicinity of a kitchen.

Incidentally, the amount of fats and oils generated in a daily life space is 0.1 mg per day·cm$^2$ (namely, about 4 $\mu$g/Hr·cm$^2$) even at a place to which extremely large amounts of fats and oils would be expected to adhere, for example, in the proximity of a ventilating fan provided at an upper part of a kitchen range in an ordinary home, as described in "Electrochemistry and Industrial Physical Chemistry", 1995, Vol.163, No. 1, p. 11. Moreover, it has been reported that a quantity of a contaminant such as tobacco nicotine and tar is not more than 0.1 mg per day·cm$^2$ (namely, about 4 $\mu$g/Hr·cm$^2$) at a living room of an ordinary home. Thus, in the case of considering the ordinary living space, 0.5 $\mu$g per day·cm$^2$ is an adequate value of the expected amount of the deposited fat and oil. Furthermore, this halogen lamp further has an advantage in that minute quantities of malodorous substances contained in an interior space or unwanted bacteria floating in the interior space are easily decomposed or annihilated when adhering to the surface of the glass container or tube of the illuminating lamp of the present invention having the self-cleaning function.

Further, a titanium dioxide film formed on the surface of the glass container is adapted in such a manner as to reduce ultraviolet light, which passes through the film and has a wavelength of a range whose center wavelength is 365 nm, by 50 to 80% and to decompose or split 1 $\mu$g or more of a linoleic acid, which is deposited on the surface of titanium dioxide film, per Hr·cm$^2$ thereof in a state in which the aforementioned light emitting portion emits light. Thereby, fats and oils deposited on the surface of the film can be decomposed. Moreover, ultraviolet light required to sterilize can be emitted to the exterior. In this case, the fat-and-oil splitting activity of this film is extremely high. Thus, the illuminating lamp can be adapted so that, even when used in the vicinity of the kitchen, the lamp is difficult to contaminate. This lamp is suitable for preventing contamination thereof by the deposited fat and oil in kitchens, in which foods are treated, of a food factory, a food restaurant, a caterer and a stuff canteen.

Film having sufficient photocatalytic activity and transmitting 50% or more of visible light, which has wavelengths of a range whose center wavelength is 550 nm, can be securely obtained by setting the film thickness of the titanium dioxide film at a value in a range of wavelengths from 0.1 to 5 $\mu$m. If the film thickness is set at a value which is less than 0.1 $\mu$m, the film sometimes cannot obtain sufficient photocatalytic activity. In contrast, if the film thickness is set at a value which exceeds 5 $\mu$m, the film sometimes cannot transmit 50% or more of visible light, which has wavelengths of a range whose center wavelength is 550 nm. In addition, the strength and abrasion resistance of the titanium dioxide film is inferior to other lamps. Moreover, the photocatalytic activity of the titanium dioxide can be further enhanced by making the film include an anatase crystal.

Further, the diffusion coating (or cementation) of a part of the ingredient of the glass container is performed by providing a precoat film between the glass container of the illuminating lamp and the titanium dioxide film. Thus, an occurrence of harmful effects such as a reduction in photocatalytic action of the titanium dioxide film can be prevented. Moreover, some latitude in choosing materials of the glass container can be enhanced. Consequently, inexpensive soda lime glass or the like can be used. Moreover, in the conventional case, when deposited directly on the glass container, it is necessary to increase the film thickness of the titanium dioxide film to the extent that, even if the material of the glass container diffuses or penetrates into the titanium dioxide film, the material thereof does not reach the titanium dioxide which performs a charge separation. However, the present invention eliminates the necessity of increasing the film thickness to such an extent. As a result, sufficient photocatalytic actions can be obtained even if the film thickness is considerably reduced, regardless of the material of the glass container.

Furthermore, if the film thickness of the precoat film is 0.02 to 1 $\mu$m, even in the case of taking materials which can be generally employed as the material of a precoat film into consideration, such film has an advantageous effect of preventing the penetration of an inhibitor, which comes from the glass container of the illuminating lamp in addition to an advantageous effect of securing the sufficient light transmittance. Conversely, if the film thickness of the precoat film is less than 0.02 $\mu$m, the effects of sufficiently preventing the penetration of an inhibitor cannot be obtained. Further, if forming a film having a thickness of more than 1.0 $\mu$m, there are no additional advantages that favor the effects of preventing the penetration. Moreover, the film deposition or formation operation becomes complex. Further, in the case of some materials, the light transmittance cannot be secured.

Usually, the best light transmittance and the effects of preventing the penetration of inhibitors is achieved by configuring the precoat film in the glass container by using a material, whose principal ingredient is $SiO_2$, as the material thereof.

At least one layer of the aforementioned precoat film is made to contain a film formed from a material made mainly of indium oxide and/or tin oxide. Thus, the illuminating lamp can have the advantageous effects of preventing a material from penetrating from the glass container of the illuminating lamp whose substrate is similar to that of $SiO_2$ film. In addition, the illuminating lamp can impart an electromagnetic wave shielding function to the glass container of this illuminating lamp owing to the conductivity originated from the indium oxide and/or the tin oxide. The present invention can prevent static electricity, which is generated when turning on the illuminating lamp, and can preventing harmful electromagnetic wave from being radiated into the space. Consequently, this lamp has merits in preventing dusts in a room from adhering thereto, and in reducing noise which exerts ill effects on electronic equipment provided in the room.

Furthermore, there is configured a window glass by comprising a titanium dioxide film, formed on at least one of sides of a glass sheet or plate, wherein the aforesaid titanium dioxide film is adapted to have a linear transmittance of 50% or more when measured by using light having a wavelength of 550 nm and to have a linear transmittance of 50% or less when measured by using light having a wavelength of 350 nm, and wherein the aforesaid titanium dioxide film has ability to decompose 0.5 $\mu$g of linoleic (or linolic) acid per square centimeter of the film for one hour in a case that the film is irradiated with ultraviolet light including at least light, whose wavelength ranges 300 to 400 nm, and having a power density of 5 $mW/cm^2$. This enables the window glass to obtain epoch-making self-cleaning performance or function by which fats and oils are effectively split or decomposed by simultaneously securing light transmittance which is sufficient for acting as a window glass. Meanwhile, when conventional window glasses are used in, for instance, a building, or transportation vehicles such as an automobile and a train, soot and tobacco tars adhere thereto. Elimination of such soot and tars is very difficult. However, in the case of the window glass of the present invention, the tobacco tars are relatively easily decomposed and eliminated by utilizing external light and indoor light simultaneously with the adhesion of the soot and tars thereto. Thus, the epoch-making window glass of the present invention can automatically maintain a predetermined clean state at all times without troubles. Needless to say, because the window glass has the ability to split or decompose fats and oils, the decomposition of which is considered in general as being very difficult, the window glass of the present invention has an antibacterial function and a deodorization function.

Titanium dioxide film, which has sufficient photocatalytic actions and linear transmittance of 50% or more corresponding to the wavelength of 550 nm, is obtained by setting the film thickness of the titanium dioxide film at 0.1 to 5 $\mu$m. In this case, if the film thickness is set at a value which is less than 0.1 $\mu$m, sufficient photocatalytic action is not obtained. Further, if the film thickness exceeds 5 $\mu$m, linear transmittance corresponding to the light having a wavelength of 500 nm is less than 50%. Thus, sufficient transparency cannot be secured.

Further, the photocatalyst activity is further enhanced by making the film contain anatase crystals. Enhancement of the photocatalytic activities, especially, the deodorization and the antibacterial activities can be achieved by adding 0.05 to 5 atom % of one element selected from a group of silver, copper and zinc to a titanium atom in the titanium dioxide film. These additives may be added thereto by various addition methods. However, in this case, a photoreduction method utilizing a photocatalytic action is easiest to perform and is most excellent. Thus, for example, in the case of adding silver, this method has an advantage in that high antibacterial activities are maintained not only when the film is irradiated with light, but also when the film is not irradiated. Further, in the case of adding zinc, the adsorption of an acidic substance to the surface thereof can be facilitated by lowering the solid acidity of titanium dioxide. Thus, this is advantageous in the decomposition and elimination.

Occurrences of evil effects, such as the degradation in photocatalytic actions, which is caused as a result of diffusion coating of a part of ingredients of a glass body into the titanium dioxide titanium film, can be prevented by providing a precoat film between the glass body and the titanium dioxide film. Further, some latitude in selecting the material of the glass body can be enhanced. Moreover, in the conventional case, when deposited directly on the glass container, it is necessary to increase the film thickness of the titanium dioxide film to the extent that, even if the material of the glass body diffuses or penetrates into the titanium dioxide film, the material thereof does not reach the titanium dioxide which performs a charge separation. However, the present invention eliminates the necessity of increasing the film thickness to such an extent. Thus, sufficient photocatalytic actions can be obtained even if the film thickness is considerably reduced, regardless of the material of the glass body.

Furthermore, if the film thickness of the precoat film is 0.02 to 1 $\mu$m, even in the case of taking materials which can be generally employed as the material of a precoat film into consideration, such film has an advantageous effect of preventing the penetration of an inhibitor, which comes from the glass container of the illuminating lamp in addition to an advantageous effect of securing the sufficient light transmittance. Conversely, if the film thickness of the precoat film is less than 0.02 $\mu$m, the effects of sufficiently preventing penetration of an inhibitor cannot be obtained. Further, if forming a film having a thickness of more than 1.0 $\mu$m there are no additional advantages that favor the effects of preventing penetration. Moreover, the film deposition or formation operation becomes complex. Further, in the case of some materials, the light transmittance cannot be secured.

Usually, the best light transmittance and the effects of preventing the penetration of inhibitors is achieved by configuring the precoat film in the glass container by using a material, whose principal ingredient is $SiO_2$, as the material thereof. Thus, the illuminating lamp can have the advantageous effects of preventing a material from penetrating from the glass body of the illuminating lamp whose substrate is similar to that of an $SiO_2$ film. In addition, the illuminating lamp can impart an electromagnetic wave shielding function to the glass body of this illuminating lamp owing to the conductivity originated from the indium oxide and/or the tin oxide. In the case of ordinary erections, such as a building, external electromagnetic waves intrude thereinto through window glasses most frequently. It is extremely valuable to impart the electromagnetic shielding function to the window glass together with the self-cleaning function.

BRIEF DESCRIPTION OF THE DRAWINGS

FIG. 3 is a diagram for showing a table in which the thickness of films of Examples according to the present invention and Comparative Examples, results of measurement of photocatalytic activities thereof and results of measurement of the light transmittance thereof are presented;

FIG. 4 is a diagram for showing a graph which represents results of measurement of fat splitting activities of Example 16 to Example 18 according to the present invention;

FIG. 7 is a diagram for showing a table in which results of measurement of the characteristics of Example 21 to Example 32 according to the present invention are presented;

FIG. 9 is a diagram for showing a table in which results of measurement of the characteristics of Example 33 to Example 39 according to the present invention and Comparative Example 4 to Comparative Example 9 are presented;

FIG. 15 is a diagram for showing a table in which results of measurement of the characteristics of Example 41 to Example 49 according to the present invention and Comparative Example 10 to Comparative Example 12 are presented.

BEST MODE FOR CARRYING OUT THE INVENTION

Example 1

Figure 1:
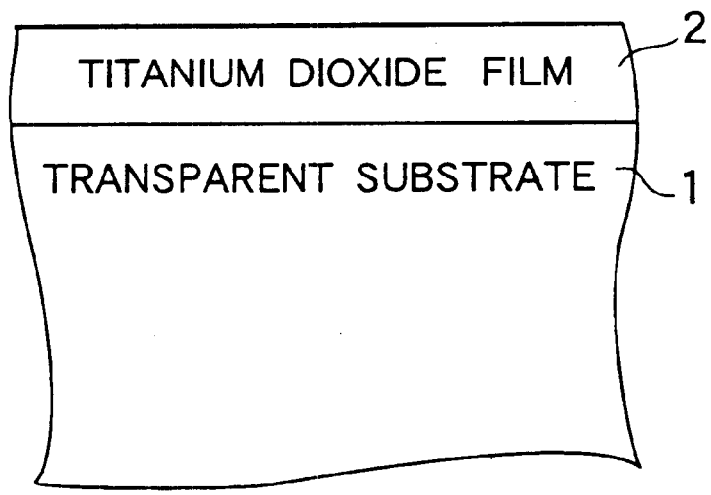
FIG. 1 is a partially sectional diagram for illustrating the configuration of a titanium dioxide photocatalyst structure according to Example 1.

FIG. 1 is a partially sectional diagram for illustrating the configuration of a titanium dioxide photocatalyst structure according to Example 1 of the photocatalyst structure of the present invention. Hereinafter, Example 1 of the titanium dioxide photocatalyst structure and a method for producing this titanium dioxide photocatalyst structure will be described with reference to FIG. 1.

As shown in FIG. 1, in the case of this example of the titanium dioxide photocatalyst structure, a titanium dioxide film 2 is formed on a transparent substrate 1.

The transparent substrate 1 is a soda lime glass substrate whose thickness, longitudinal size and lateral size are 1, 100 and 50 mm, respectively.

The film 2 is a titanium dioxide film which contains anatase crystals and is 4.8 $\mu$m in thickness.

The aforementioned titanium dioxide photocatalyst structure was produced by performing the following process.

First, a transparent substrate 1 was produced by extracting a soda lime glass whose thickness, longitudinal size and lateral size were 1 mm, 100 mm and 50 mm, respectively.

Next, a raw-material solution, in which the concentration of titanium isopropoxide was adjusted to 0.5 mol/L, was made by dissolving titanium isopropoxide in acetylacetone solvent as the material of a titanium dioxide film.

Subsequently, the transparent substrate 1 was set in a pyro-sol film forming device. Further, the transparent substrate 1 was preliminarily heated to 500 degrees centigrade. Moreover, the raw-material solution underwent ultrasonic atomization and was then introduced to the surface of the transparent substrate 1 at a rate of 20 mL/min. Then, an operation of forming a film was performed in the period of about 60 minutes. Consequently, there had been obtained a titanium dioxide photocatalyst structure in which this titanium dioxide 2, whose thickness was 4.8 $\mu$m, was formed on the transparent substrate 1. Incidentally, according to a result of analysis of this titanium dioxide film 2 based on X-ray diffraction, it was verified that this film 2 contained anatase crystals.

Next, the photocatalytic activity and light transmittance of the obtained titanium dioxide photocatalyst structure were measured by performing the following method.

Method for Measuring Photocatalytic Activity

The titanium dioxide photocatalyst structure was placed in the bottom of a cylindrical glass gastight enclosure, whose capacity was 1.5 L, in such a way that the titanium dioxide film 2 was the upper part thereof. Then, acetaldehyde was introduced into this enclosure so that the concentration of acetaldehyde was 1300 ppm. Next, the titanium dioxide photocatalyst structure was irradiated with light from above the surface of the titanium dioxide film 2 by using three 10-W black lights. At that time, the illuminance measured on the surface of the titanium dioxide film 2 was 1.2 mW/cm$^2$. Thereafter, the quantitative analysis of acetaldehyde contained in the glass gastight enclosure was performed by using a gas chromatograph with FID. Thus, the decrement of the amount of acetaldehyde, which was caused after the photocatalyst structure was irradiated with light, was obtained. Further, the obtained decrement of the amount of acetaldehyde was defined as the degree of the photocatalytic activity.

Method for Measuring Light Transmittance

Titanium dioxide photocatalyst structure of Example 1 was first set in a device for measuring light transmittance (namely, UV-3100PC manufactured by Shimadzu Corporation). Then, the light transmittance corresponding to light, whose wavelength is 550 nm, was measured.

According to a result of the measurement by the hereinaforementioned method, what is called the decomposition activity was 10.5 $\mu$l/min and the light transmittance was 70%. Thus, it was verified that this titanium dioxide photocatalyst structure had excellent photocatalytic activity and sufficient transparency.

Then, the titanium dioxide photocatalyst structure was again placed in the bottom of the aforesaid cylindrical glass gastight enclosure by being turned upside down, namely, in such a way that the titanium dioxide film 2 faced the bottom of the enclosure. Subsequently, the photocatalytic activity of the photocatalyst structure was measured by irradiating the photocatalyst with light coming from the similar direction, namely, from the side, on which the titanium dioxide film 2 was not formed, of the transparent substrate 1. At that time, it was verified that the photocatalytic activity, whose value was nearly close to that obtained in the aforementioned case, could be obtained. This result shows that light applied from the back surface of the transparent substrate 1 contributes to the photocatalytic activity of the titanium dioxide film 2 as well as the light applied from the front surface of the transparent substrate 1 and that the photocatalytic effects thereof can be considerably enhanced by applying light to both sides of the photocatalyst structure.

Example 2 to Example 6

These Examples have structures, which are similar to the structure of Example 1 except that the thickness of the titanium dioxide film 2 is different from that of the film 2 of Example 1, and are produced by a producing method similar to that employed in the case of Example 1. Data representing the thickness of each Example and results of measurement of the photocatalytic activity and light transmittance are shown in FIG. 3 in tabular form. Further, the detailed description of the data is omitted.

As is seen from the table of FIG. 3, each of these Examples has excellent photocatalytic activity and sufficient transparency.

Example 7 to Example 12

Figure 2:
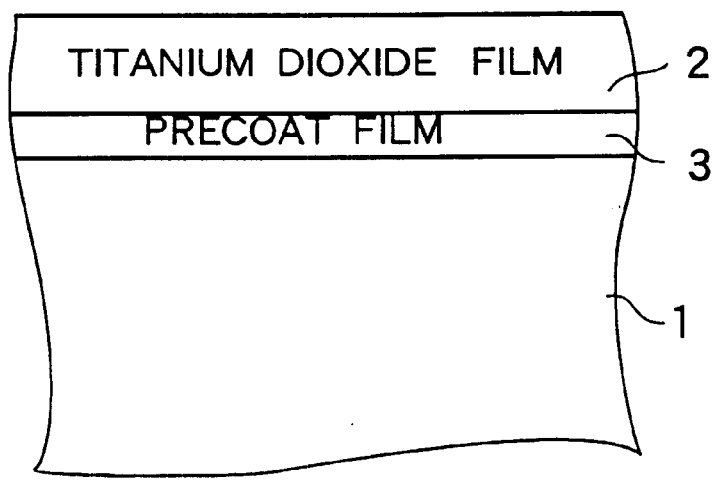
FIG. 2 is a partially sectional diagram for illustrating the configuration of a titanium dioxide photocatalyst structure according to Example 7.

These Examples have structures, which are similar to the structure of Example 1 except that a precoat film 3 constituted by a $SiO_2$ film is formed between the titanium dioxide film 2 and the transparent substrate 1 by a dip coating as illustrated in FIG. 2, and are produced by a producing method similar to that employed in the case of Example 1. Data representing the thickness of each Example and results of measurement of the photocatalytic activity and light transmittance are shown in FIG. 3 in tabular form. Further, the detailed description of the data is omitted.

As is seen from the table of FIG. 3, even when the thickness of the titanium dioxide film 2 is reduced, excellent photocatalytic activities are exhibited, in comparison with Example 1 to Example 6 which do not have the precoat film 3. Thus, further higher transparency can be ensured.

Example 13 to Example 14

These Examples have structures, which are similar to the structure of Example 1 except that the soda lime glass of Example 1 is replaced with quartz glass, and are produced by a producing method similar to that employed in the case of Example 1. Data representing the thickness of each Example and results of measurement of the photocatalytic activity and light transmittance are shown in FIG. 3 in tabular form. Further, the detailed description of the data is omitted.

As is seen from the table of FIG. 3, even though the Examples do not have the precoat film 3, excellent photocatalytic activities are exhibited, because quartz glass is used as the material of the transparent substrate 1. In addition, these Examples have sufficient transparency.

Example 15

This Example has a structure, which is similar to the structure of Example 1 except that the temperature at the time of forming the titanium dioxide film is changed into 380 degrees centigrade and that the step of performing heat treatment in the period of 60 minutes at the temperature of 400 degrees centigrade under air atmosphere is added, and are produced by a producing method similar to that employed in the case of Example 1. Data representing the thickness of each Example and results of measurement of the photocatalytic activity and light transmittance are shown in FIG. 3 in tabular form. Further, the detailed description of the data is omitted. As is seen from the table of FIG. 3, each of these Examples has excellent photocatalytic activity and sufficient transparency.

Example 16

In the case of this Example, the precoat film 3 constituted by a SiO2 film having a thickness of 0.06 µm was formed on the transparent substrate 1. Moreover, the titanium dioxide film 2 having a thickness of 0.8 µm was formed by what is called a dipping method.

A soda lime glass plate, whose thickness, longitudinal size and lateral size are 1 mm, 100 mm and 50 mm, respectively, was used as the transparent substrate 1. This transparent substrate 1 was slowly dipped into a vessel, which contains silicon alkoxide solution (incidentally, the trade name thereof was "ATOLON NSi-500" and was manufactured by Nippon Soda Co., Ltd.) of 800 ml and has a width of 100 mm, a depth of 50 mm and a height of 200 mm, respectively. Thereafter, this transparent substrate 1 was pulled up therefrom at a speed of 10 cm/min. This substrate was then dried at the temperature of 150 degrees centigrade. Subsequently, the substrate was sintered at the temperature of 500 degrees centigrade in the period of 1 hour. Thus, a $SiO_2$ film, whose thickness was 0.06 µm, was formed on the transparent substrate 1 as the precoat film 3.

Next, the glass substrate provided with the precoat film was slowly dipped into 800 ml of an organic titanium solution for dipping (incidentally, the trade name thereof was "ATOLON NTi-500" and was manufactured by Nippon Soda Co., Ltd.), which was obtained by causing titanium tetraisoproxide to react with organic solvent. Thereafter, the substrate was slowly pulled up therefrom at a speed of 10 cm/min. This substrate was then dried at the temperature of 120 degrees centigrade. Subsequently, the substrate was sintered at the temperature of 500 degrees centigrade in the period of 1 hour. Thus, a titanium dioxide film was formed on the precoat film. This process for forming a titanium dioxide film, which had the steps of dipping the substrate into chemicals and then drying and sintering the substrate, was repeated 10 times. Thus, the thickness of the titanium dioxide became 0.8 µm, so that the titanium dioxide photocatalyst structure of this Example was obtained.

The titanium dioxide photocatalyst structure obtained in this way has the light transmittance of 81% correspondingly to light having the wavelength of 550 nm. Further, regarding this Example, a fat splitting activity was taken up as one of the photocatalytic activities and was evaluated as follows.

Evaluation of Fat Splitting Activity

The aforementioned titanium dioxide photocatalyst structure was extracted as a 50-by-50-mm test piece. Then, the entire surface of the test piece was softly wiped with tissue paper which had soaked commercially available salad oil. Thus, an amount of applied salad oil was adjusted to 0.1 mg/cm² by applying the salad oil thereto and wiping the salad oil therefrom. The initial amount of salad oil was measured by weighing the glass plate by using a precision balance whose weight accuracy is 0.1 mg. This substrate, to which the salad oil had been applied, was then irradiated with ultraviolet rays coming from ultraviolet lamps (namely, three 10-W black lights FL10BLB manufactured by Matsushita Electric Works, Ltd. arranged in a low and used for applying the ultraviolet rays) for a predetermined time period, by regulating the distance between each ultraviolet lamp and the surface of the test piece in such a manner that the ultraviolet intensity measured by the ultraviolet-intensity detector (manufactured by Ultraviolet Corporation) was 3 mW/cm$^2$. After the predetermined time period has passed, the amount of the split salad oil (fat) was found by measuring the weight of the glass substrate.

FIG. 4 illustrates a graph which shows the fat splitting characteristics of the photocatalyst structure of Example 16. Incidentally, in the graph of FIG. 4, the vertical axis represents the rate of residual fat (in %); and the horizontal axis a time period in which ultraviolet was applied (in hours). Further, similarly as in the herein-aforementioned case, salad oil was applied to the glass substrate provided only with a precoat film, on which no titanium dioxide film was formed. Then, ultraviolet was applied thereto (from the black light). After the predetermined time period passed, a change in weight of the glass substrate was measured. Thus, the resultant data was obtained as data in the case of a "blank" test piece. The result in this case is also shown in the graph of FIG. 4. As is obvious from FIG. 4, this titanium dioxide photocatalyst structure has excellent fat splitting activity.

Example 17

In the case of this Example, the precoat film 3 constituted by a SiO$_2$ film having a thickness of 0.06 μm was formed on the transparent substrate 1. Further, a titanium dioxide film having a thickness of 0.6 μm was formed thereon by performing what was called a spraying method.

Similarly as in the case of Example 16, the SiO$_2$ film having a thickness of 0.06 μm was formed as the precoat film 3 by using a soda lime plate whose thickness, longitudinal size and lateral size are 1 mm, 100 mm and 50 mm, respectively.

Next, the transparent substrate 1, on which this precoat film 3 was formed, was leaned against the inner part of a box-type heater which had been heated to 500 degrees centigrade. Then, 10 shots of an organic solvent solution of titanium acetylacetonato obtained by causing a reaction between 140 g of titanium tetraisopropoxide and 200 g of acetylacetone were sprayed onto the precoat film 3 of the transparent substrate 1. Subsequently, the titanium dioxide film 2 having a thickness of 0.6 μm was formed by performing thermal decomposition thereon.

Figure 14:
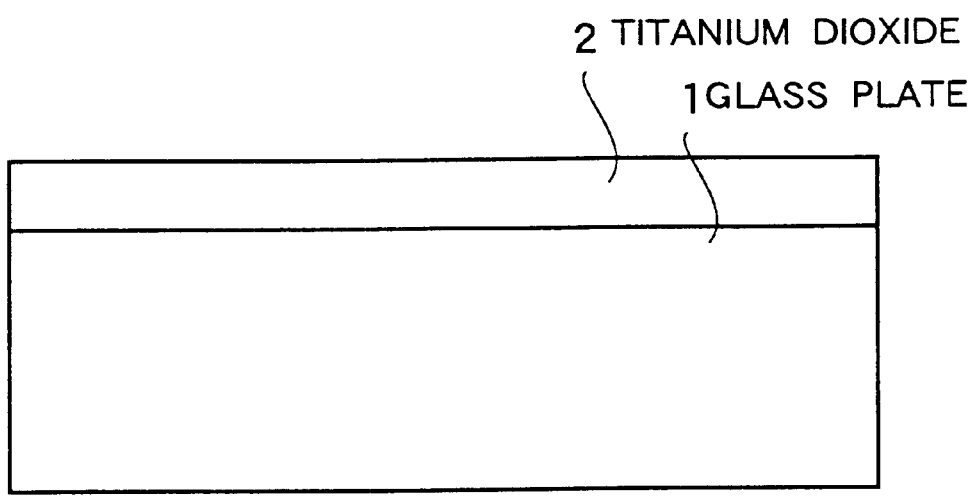
FIG. 14 is a sectional view of a window glass of Example 41 according to the present invention.

The light transmittance of the titanium dioxide photocatalyst structure corresponding to light having the wavelength of 550 nm was 78%. Further, the fat splitting activity acting as the photocatalytic activity was measured similarly as in the case of Example 16. A result of this measurement is shown in FIG. 14 together with a result of the measurement in the case of Example 16.

Example 18

In the case of this Example, the precoat film 3 constituted by a SiO$_2$ film having a thickness of 0.06 μm was formed on the transparent substrate 1. Further, a titanium dioxide film having a thickness of 0.4 μm was formed thereon by performing what was called a printing method.

Similarly as in the case of Example 16, the SiO$_2$ film having a thickness of 0.06 μm was formed as the precoat film 3 by using a soda lime plate whose thickness, longitudinal size and lateral size are 1 mm, 100 mm and 50 mm, respectively.

Next, a screen process printing was performed by a printing machine, which was provided with a 400-mesh screen, on the aforementioned precoat film 3 by using a solvent obtained by causing a reaction and dissolution among 70 g of titanium tetraisopropoxiode, 10 g of ethyl cellulose and 1200 g of organic solvent. Upon completion of printing, the film was put into a stationary state in the period of 5 min. Then, the leveling of the film was performed. Thereafter, the film was sintered in an electric furnace which had been heated to 500 degrees centigrade. This printing and sintering process was repeated 5 times. Thus, the thickness of the titanium dioxide became 0.4 μm, so that the titanium dioxide photocatalyst structure of this Example was obtained.

The light transmittance of this photocatalyst structure corresponding to the wavelength of 550 nm was 86%. Further, similarly as in the case of Example 16, the fat splitting activity was measured. Thus, a result of this measurement was obtained as shown in the graph of FIG. 4.

Example 19

In the case of this Example, the precoat film 3 constituted by a SiO$_2$ film having a thickness of 0.04 μm was formed on the transparent substrate 1 by performing the pyro-sol method. Moreover, the titanium dioxide film 2 having a thickness of 0.4 μm was formed thereon by the dipping method.

The transparent substrate 1 constituted by a soda lime glass plate, whose thickness, longitudinal size and lateral size are 1 mm, 100 mm and 50 mm, respectively, was set in the pyro-sol film forming device. Subsequently, organic silicon solution (incidentally, the trade name thereof was "ATOLON NSi-500" and was manufactured by Nippon Soda Co., Ltd.) underwent ultrasonic atomization and was then introduced to the glass substrate, which had been heated to 500 degrees centigrade, at a rate of 20 mL/min in the time period of 2 min. Thus, the silicon-dioxide precoat film 3, whose thickness was 0.04 μm, was formed.

Next, similarly as in the case of Example 16, a titanium dioxide film was formed on this precoat film 3 by performing the dipping method. This process for forming a titanium dioxide film, which had the steps of dipping the substrate into chemicals and then soaking, drying and sintering the substrate, was repeated 5 times. Thereby, the thickness of the titanium dioxide became 0.4 μm, so that the titanium dioxide photocatalyst structure, in which the transparent titanium dioxide film 2 was formed, was obtained.

Figure 5:
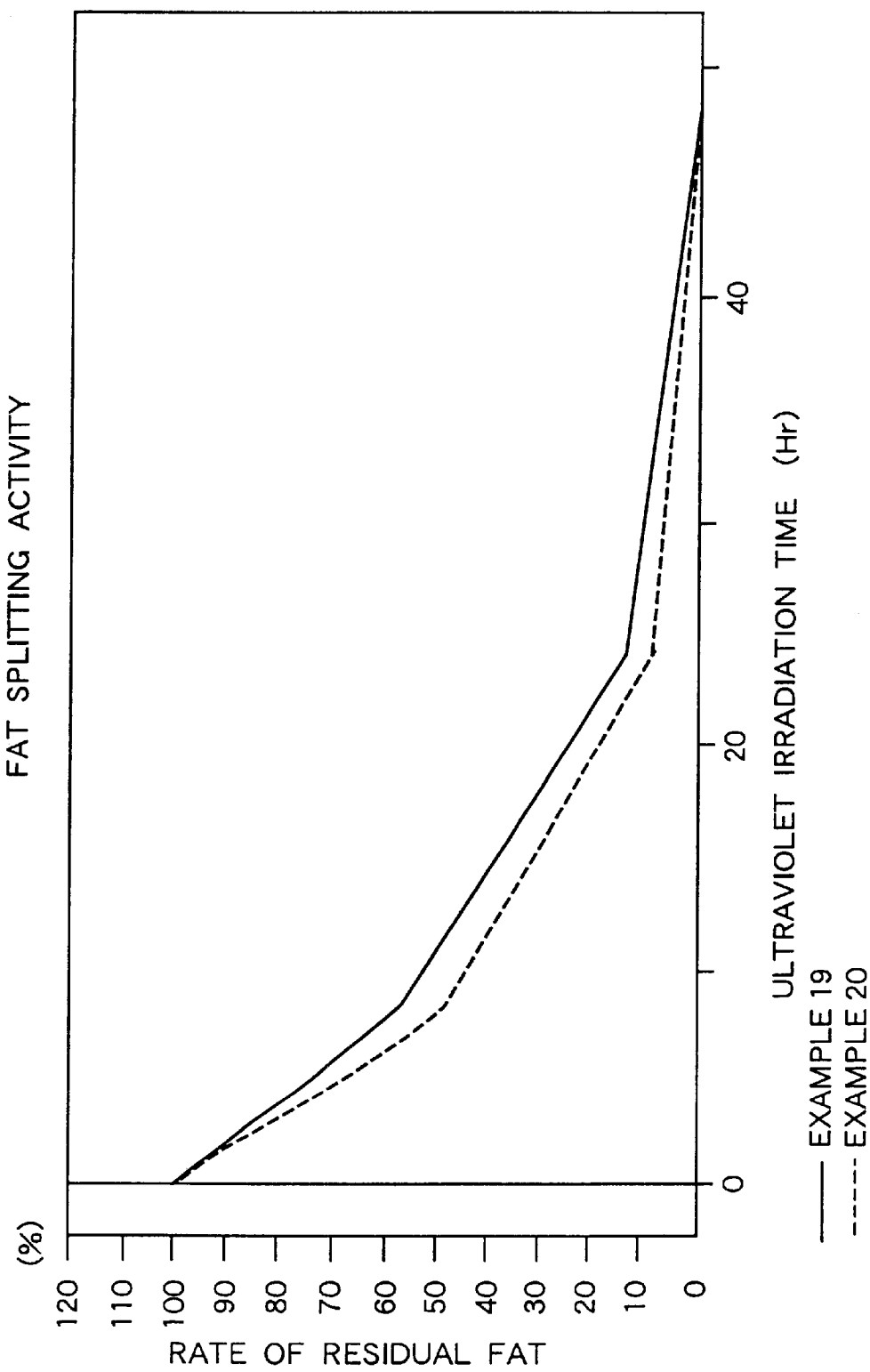
FIG. 5 is a diagram for showing a graph which represents results of measurement of fat splitting activities of Example 19 and Example 20 according to the present inventions.

The light transmittance of this photocatalyst structure corresponding to the wavelength of 550 nm was 89%. Further, similarly as in the case of Example 16, the fat splitting activity was measured. Thus, a result of this measurement was obtained as shown in the graph of FIG. 5.

Example 20

In the case of this Example, the precoat film 3 constituted by a SiO$_2$ film having a thickness of 0.06 μm was formed on the transparent substrate 1. Moreover, the titanium dioxide film 2 having a thickness of 0.6 μm was formed thereon by what is called a CVD method.

The transparent substrate 1 constituted by a soda lime glass plate, whose thickness, longitudinal size and lateral size are 1 mm, 100 mm and 50 mm, respectively, was used as the transparent substrate 1. Moreover, the precoat film 3, which was made of silicon dioxide and was 0.06 μm in thickness, was formed by performing the same method as used in the case of Example 16.

Next, the transparent substrate 1, on which this precoat film 3 was formed, was set in an atmospheric pressure CVD film forming device. Further, titanium tetraisopropoxide was prepared in a carbureter heated to 200 degrees centigrade. Then, gaseous nitrogen was introduced into the carbureter at the flow rate of 50 ml/min to thereby cause the bubbling of titanium tetraisopropoxide. Subsequently, the vapor of titanium alkoxide was introduced through a heated conduit into a film forming portion in which the glass substrate was set. The film forming portion was heated to 500 degrees centigrade. Furthermore, air was also introduced thereinto at the rate of 200 ml/min. Thus, an operation of forming a film was performed in the period of 5 minutes. Thereby, the titanium dioxide film 2 having a thickness of 0.6 μm was formed on the precoat film 3, so that the titanium dioxide photocatalyst structure was obtained.

The light transmittance of this photocatalyst structure corresponding to the wavelength of 550 nm was 89%. Further, similarly as in the case of Example 16, the fat splitting activity was measured. Thus, a result of this measurement was obtained as shown in the graph of FIG. 5.

Comparative Example 1

This Comparative Example has a structure, which is similar to the structure of Example 1 except that the thickness of the titanium dioxide film 2 is small, namely, 0.05 μm, and was produced by a producing method similar to that employed in the case of Example 1. Data representing the thickness of this Comparative Example and results of measurement of the photocatalytic activity and light transmittance are shown in FIG. 3 in tabular form. Further, the detailed description of the data is omitted.

As is seen from the table of FIG. 3, this Comparative Example has good transparency but exhibits little photocatalytic activity.

Comparative Example 2

This Comparative Example has a structure, which is similar to the structure of Example 1 except that the temperature at the time of forming the titanium dioxide film was changed into 380 degrees centigrade, and was produced by a producing method similar to that employed in the case of Example 1. Data representing the thickness of this Comparative Example and results of measurement of the photocatalytic activity and light transmittance are shown in FIG. 3 in tabular form. Further, the detailed description of the data is omitted. Incidentally, according to a result of analysis of the titanium dioxide film 2, which was produced in this way, based on X-ray diffraction, it was verified that this film 2 did not contained anatase crystals at all.

As is seen from the table of FIG. 3, this Comparative Example has sufficient transparency but exhibits little photocatalytic activity.

Comparative Example 3

This Example has a structure, which is similar to the structure of Example 1 except that the titanium dioxide film 2 was formed by using a method of applying 0.1 g of a solution, which was obtained by dispersing titanium dioxide powder (namely, "P-25" manufactured by NIPPON AEROSIL CORPORATION) into water, to the substrate, instead of the pyro-sol method, and was produced by a producing method similar to that employed in the case of Example 1. Data representing the thickness of this Comparative Example and results of measurement of the photocatalytic activity and light transmittance are shown in FIG. 3 in tabular form. Further, the detailed description of the data is omitted.

As is seen from the table of FIG. 3, this Comparative Example has high photocatalytic activity but has little transparency.

Example 21

Figure 6:
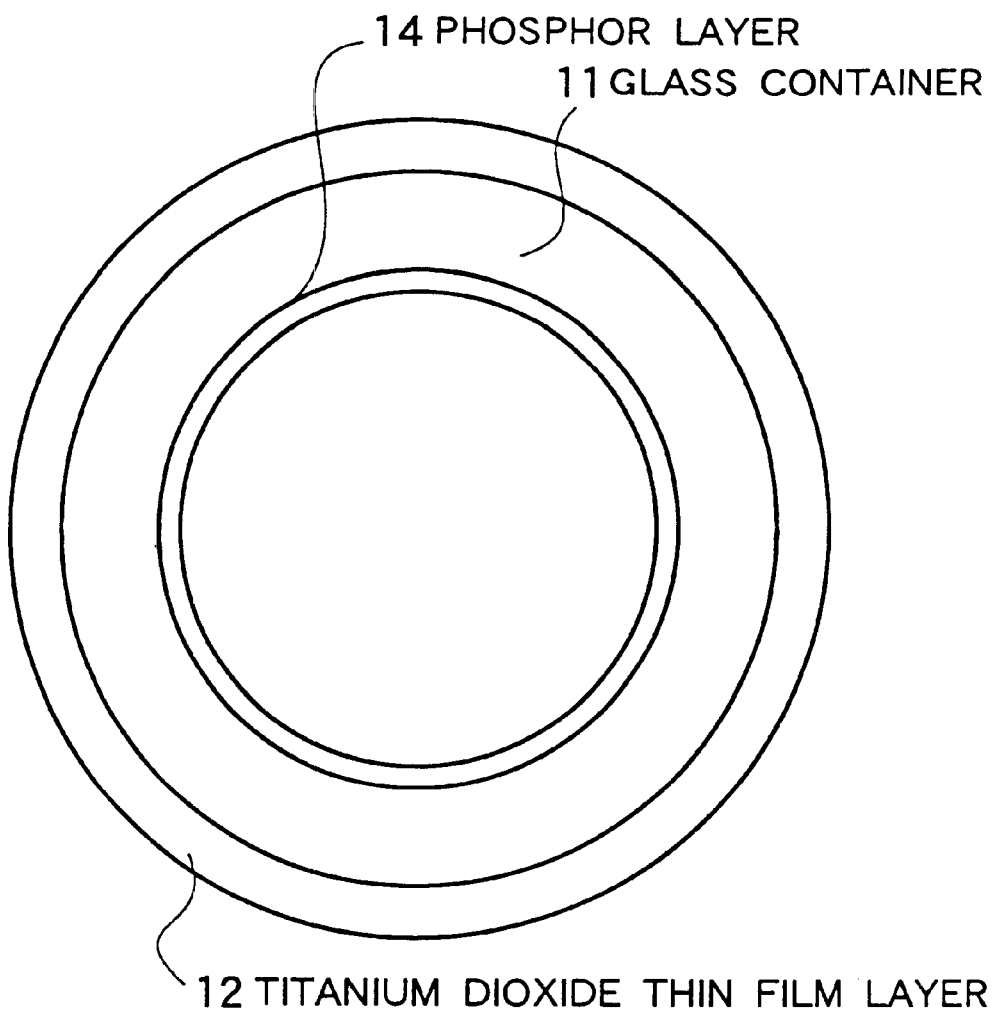
FIG. 6 is a sectional view of a lighting device of Example 21 according to the present invention.

FIG. 6 is a sectional view of an illuminating lamp which is Example 21 of the present invention. Hereinafter, by referring to FIG. 6. Incidentally, this Example is constituted by a fluorescent light or lamp.

In this figure, reference numeral 11 designates a cylindrical glass container that has an inner wall surface, onto which a phosphor (or fluorescent material) layer 14 is applied, and an outer wall (namely, the (outer) surface of the glass container), on which a titanium dioxide film is formed. Further, necessary (filler) gases are encapsulated in the inside of the glass container 11, similarly as in the case of a known fluorescent lamp. Moreover, both end portions (not shown) of the glass container, namely, both of the end portions provided in a direction perpendicular to paper, on which this figure is drawn, are sealed. Furthermore, electrodes (not shown) necessary for constructing the known fluorescent lamp are provided thereat, respectively. Light emitting portion is constituted by these elements, namely, the phosphor layer 14 and the filler gas.

Glass container 11 is 25.5 mm in outside diameter, 23.0 mm in inside diameter and 330 mm in length and is a 10-W fluorescent lamp.

Titanium dioxide film 12 contains anatase crystals and is 4.7 μm in thickness.

This illuminating lamp was manufactured as follows.

First, the glass container 11 for a 10-W fluorescent lamp, in which was 25.5 mm in outside diameter, 23.0 mm in inside diameter and 33.0 mm in length, was set in a pyro-sol film forming device. Then, a raw material solution obtained by dissolving 0.5 mol of titanium tetraisoproxide in 1L of acetylacetones was atomized by ultrasonic waves and was then introduced into the aforementioned film forming device, wherein a film forming operation was performed at 500 degrees centigrade for about 80 minutes. Thus, a titanium dioxide film was formed on the glass container 11 for the fluorescent lamp.

It is verified by a scanning electron microscope (SEM) and an energy dispersive x-ray spectrometer (EDS) that this film 12 was a titanium dioxide film which was 4.7 μm in thickness. Moreover, a part of this glass container was cut off and then, a film was analyzed by a film X-ray diffraction. This analysis revealed that the film contained an anatase crystal.

Next, a phosphor layer 14 was formed by applying a phosphor onto the inner wall of the glass container 11 on which a titanium dioxide film 12 was formed. Then, electrodes were inserted into the both end portions of the glass container. Subsequently, the container was sealed and is vacuum-pumped through an exhaust tubing or capillary. Thereafter, the glass container was filled with an argon gas at a pressure of 5 Torr and a minute amount of mercury and was further sealed by a heat press. Thus, the illuminating lamp of this Example was obtained.

Next, the visible light illuminance, the ultraviolet light intensity (or power density) and data concerning the fat-and-oil splitting function of the illuminating lamp obtained in this way were measured. Further, similar measurement was performed by using other illuminating lamps (namely, comparative examples), each of which had the same configuration as of this example except for the presence of the titanium dioxide film and the difference in the film thickness. Indicators for evaluation of the characteristics and the performance of photocatalytic activity were obtained by making comparisons between results of the measurements performed on this example and the comparative examples. Further, the result of the measurement performed on this example is presented in a table of FIG. 7 together with the results of the measurement performed on each of the other examples.

Incidentally, the visible light illuminance, the ultraviolet light intensity (or power density) and data concerning the fat-and-oil splitting function were measured by performing processes which will be described hereinbelow.

Method of Measuring Visible Light Illuminance

After set in a lighting tool, the illuminating lamp was turned on by being energized. Then, the illuminance of visible light having wavelengths in a range, whose center wavelength was 550 nm, was measured by means of a digital illuminance meter LX-1330 manufactured by CUSTOM CORPORATION (incidentally, the wavelength-sensitivity characteristic of a silicon photodiode is shown in FIG. 5) by setting the distance between the illuminating lamp and a sensor portion at 15 cm.

Method of Measuring Ultraviolet Light Intensity

Figure 11:
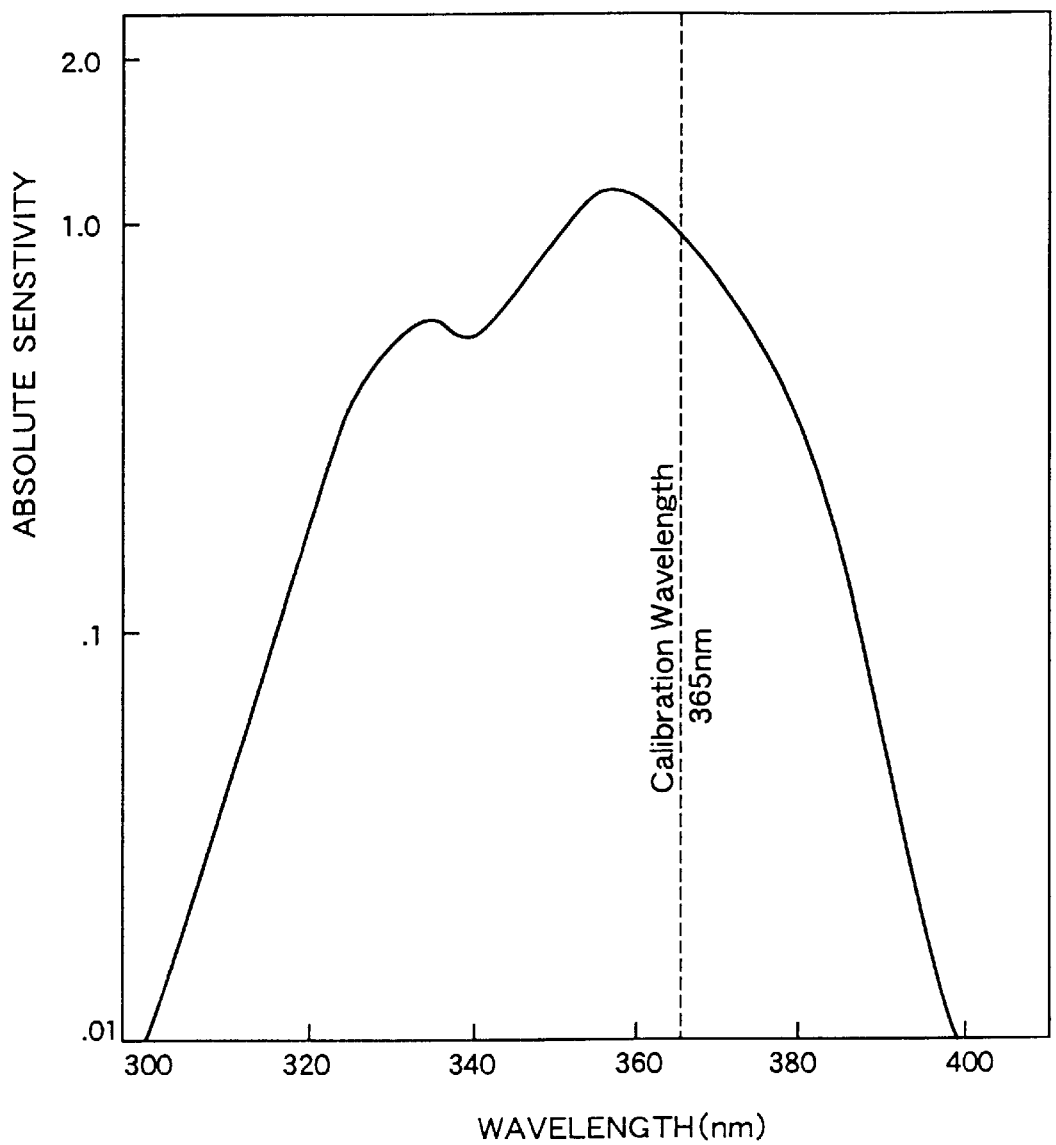
FIG. 11 is a graph showing a wavelength-sensitivity curve of a sensor for measuring the intensity (or power density) of ultraviolet light.

Similarly, the illuminating lamp was set in the lighting tool and was then turned on by being energized. Subsequently, the intensity (or power density) of ultraviolet light having wavelengths in a range, whose center wavelength was 365 nm, was measured by means of a digital ultraviolet intensity meter of the UVX-36 type (manufactured by Ultraviolet Corporation (incidentally, of the UV sensor is shown in FIG. 11))

Method of Measuring Data concerning Fat-and-Oil Splitting Function

Quantity of fats and oils split, which adhere to the surface of the lamp, when turning on the illuminating lamp was determined as an indication, which was used for evaluation of the anti-fouling function, by using salad oil, which contained linoleic acid as a major ingredient, so as to measure how fast the fat and oil was split. Namely, first, 1 to 0.15 g of salad oil was applied onto an area of 1 cm$^2$ of the surface of each lamp. The amount of the applied salad oil was obtained by measuring the weight of the lamp before and after the application of the salad oil. After turning on the lamp, the weight of the lamp was measured at predetermined moments so as to find the relation between the elapse of time and a reduction in weight of the lamp. This relation is employed as an indication (or indicator) representing the splitting activity.

As listed in the table of FIG. 7, the results of the measurement of Example 21 by the aforementioned methods were as follows: Namely, the salad-oil splitting activity was not more than 5.4 μm per day·cm$^2$; the illuminance of the visible light having wavelength of a range whose center wavelength was 1240 lux; the intensity (or power density) of the ultraviolet light having wavelength of a range whose center wavelength was 365 nm was 0.036 cm$^2$.

As is obvious from the comparison with this example, Example 21 has the splitting activity by which stain in the ordinary living space can be decomposed sufficiently. Moreover, harmful ultraviolet is reduced to 8% by being cut off (namely, a decreasing ratio is 92% ). However, as a result of providing the titanium dioxide film, the visible light illuminance is a little reduced to 82% (namely, a decreasing ratio is 18% ). Thus, it is concluded that Example 21 has extremely excellent performance.

Example 22 to Example 24

Each of these examples (or embodiments) has a configuration similar to the configuration of Example 22 except that the film thickness thereof is changed from the thickness of Example 22. Further, Example 21 to Example 24 are produced by performing methods which are similar to a method of making Example 21. Therefore, results of the measurement of the salad oil splitting activities, the illuminance of the visible light having wavelength of a range whose center wavelength was 550 nm, and the intensity (or power density) of the ultraviolet light having wavelength of a range whose center wavelength was 365 nm are listed in a table of FIG. 7, and the detailed description of these examples is omitted.

As is seen from the table of FIG. 7, each of Example 22 to Example 24 has excellent fat-and-oil splitting activity and sufficient light transmittance.

Example 25 to Example 27

Figure 8:
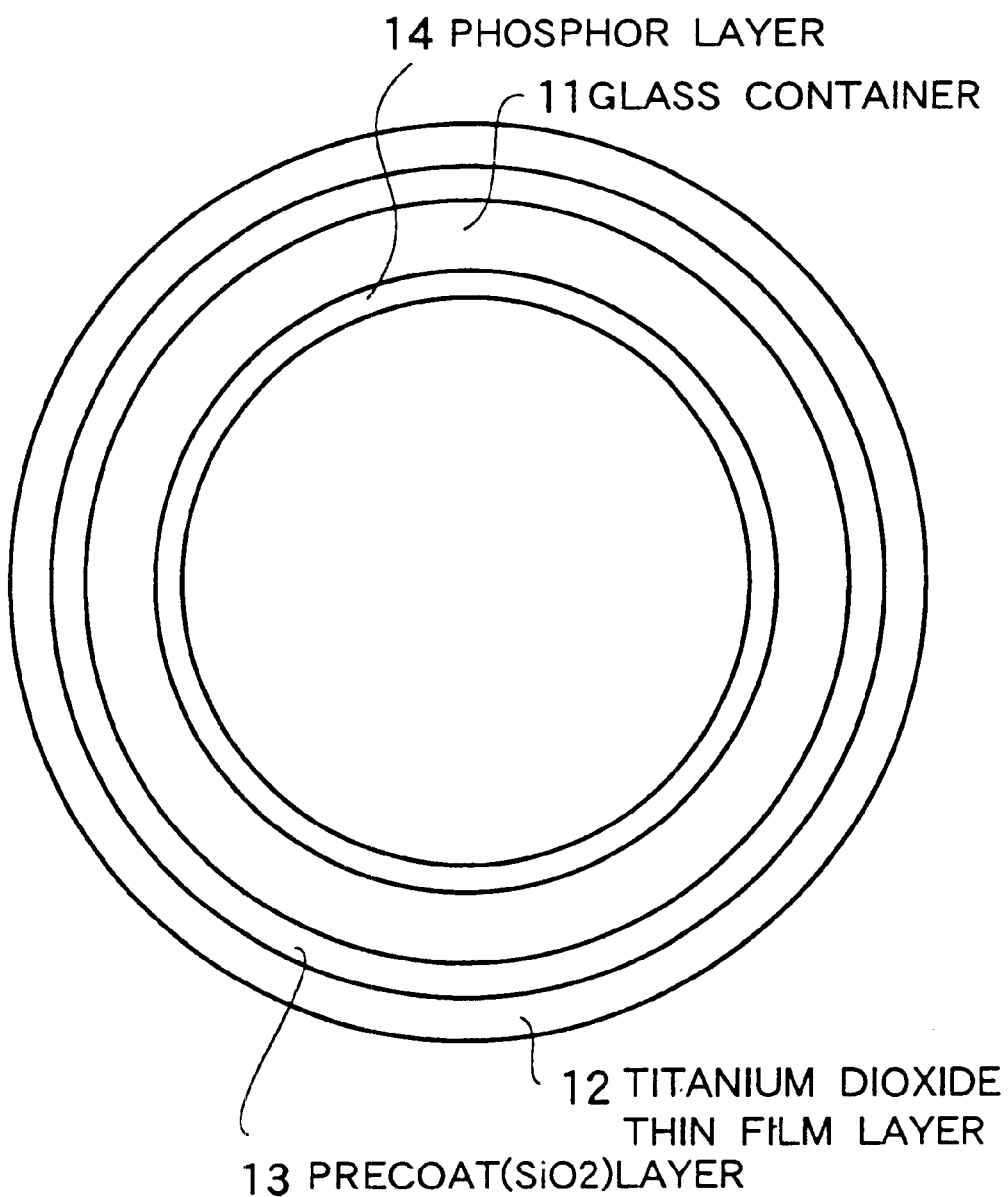
FIG. 8 is a sectional view of an illuminating device of Example 25 according to the present invention.
Figure 10:
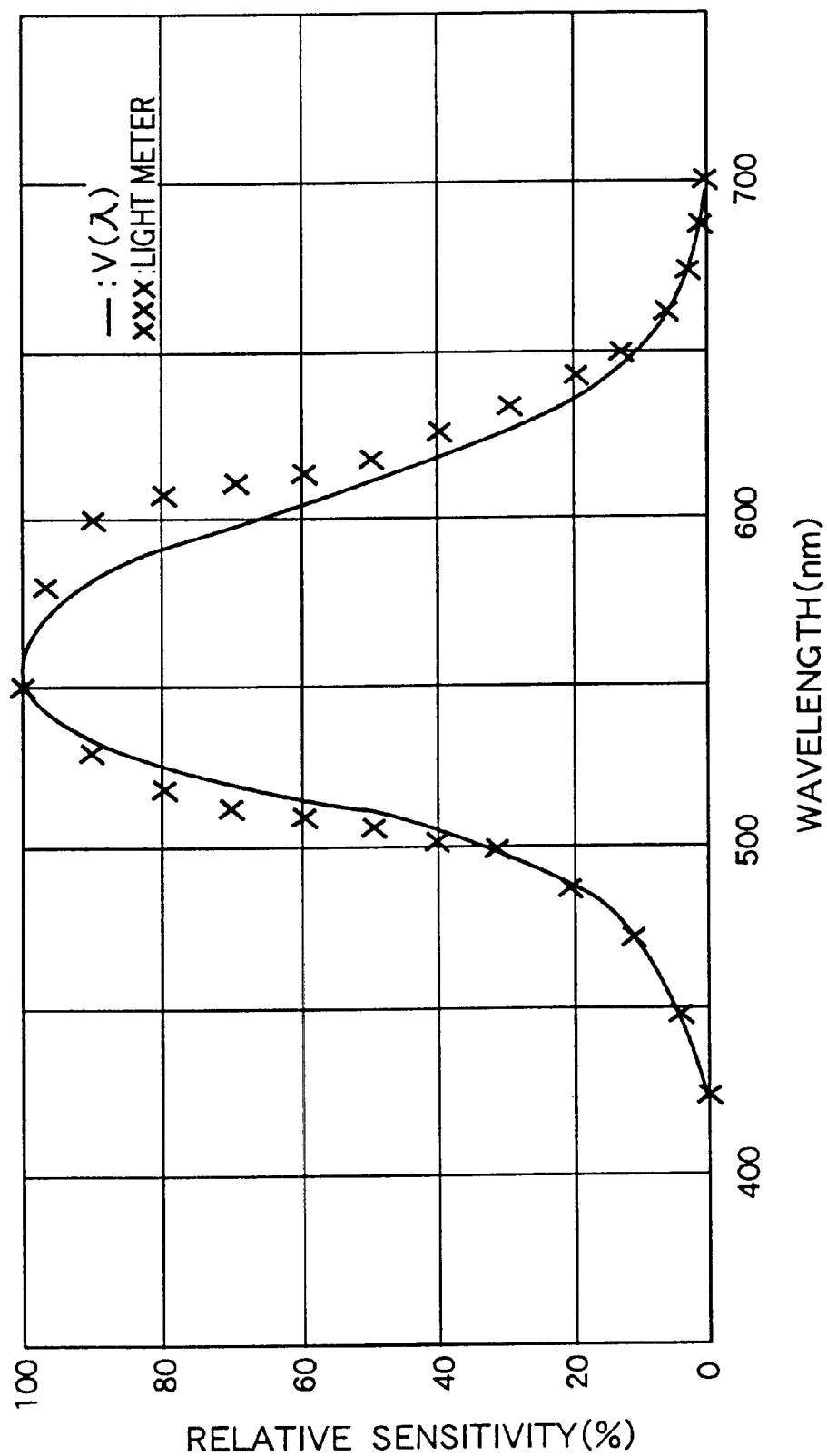
FIG. 10 is a graph showing a wavelength-sensitivity curve of a sensor for measuring the illuminance of visible light.

As illustrated in FIG. 8, these examples had configurations similar to that of Example 21 and were formed by methods similar to the method, by which Example 21 was formed, except that a precoat layer 13 constituted by a SiO$_2$film is formed between the titanium dioxide film 12 and the glass container 11 by dipcoating. Thus, the thickness in the case of these Examples, and results of the measurement of the salad oil splitting activities, the illuminance of the visible light and the intensity (or power density) of the ultraviolet light in the case of these Examples are listed in the table of FIG. 7, and the detailed description of these examples is omitted.

As described in the table of FIG. 7, Example 25 to Example 27 exhibited outstanding salad-oil splitting activities even when the thickness of the titanium dioxide film 12 was reduced, in comparison with Example 21 to Example 24 each of which was not provided with the precoat layer. Therefore, it is understood that Example 25 to Example 27 can secure higher visible light illuminance.

Example 28

This Example 28 was obtained by forming a precoat layer 13 constituted by a SiO$_2$ film between the titanium dioxide film 12 and the glass container 11 of Example 21 through a dipcoating process, and by further forming a titanium dioxide film 12 thereon similarly through the dipcoating process, as illustrated in FIG. 8. The rest of the composing elements of Example 28 were similar to the corresponding elements of Example 21.

Titanium dioxide film 12 was formed as follows. Namely, the titanium dioxide film 12, which was 1.5 μm in thickness, was formed by repeatedly performing the following operation sixteen times, namely, an operation of slowly pulling up the glass container 11, which was obtained by sealing end portions thereof and forming the precoat layer 13 therein, at a speed of 0.5 cm/sec after dipping the glass container 11 in a raw material solution obtained by dissolving 0.5 mol of titanium tetraisoproxide in 1L of acetylacetone, and of drying the pulled-up glass container at room temperature and then baking the dried glass container at a temperature of 450 degrees centigrade.

Incidentally, results of the measurement of the salad oil splitting activities, the illuminance of the visible light and the intensity (or power density) of the ultraviolet light are listed in the table of FIG. 7.

Example 29

This was an example in which the precoat layer 13 was constituted by a two-layer film. The remaining composing elements of this example, which were other than this precoat layer 13, were almost the same as the corresponding composing elements of the aforementioned Examples 25 to 27. Therefore, the detailed description of the remaining composing elements is omitted herein. This Example 29 was obtained by performing a method similar to the method used in the case of Example 25 to Example 27 as follows. Namely, a first precoat layer 13 constituted by a SiO2 film was formed between the titanium dioxide film 12 and the glass container 11 through a dipcoating process. Subsequently, a film constituted by an indium tin oxide (ITO) film including tin oxide by 8% was formed by a pyro-sol device so that the thickness of this film was 0.2 $\mu$m. Thereafter, the titanium dioxide film 12 was provided by performing the similar method as performed in the case of Example 21. Incidentally, results of the measurement of the salad oil splitting activities, the film thickness of each of the first and second precoat layers, the illuminance of the visible and the intensity (or power density) of the ultraviolet light are listed in the table of FIG. 7.

As is seen from the table of FIG. 7, in comparison with the case of the titanium dioxide films of Example 25 to Example 27 which have no precoat layers, a thinner film exhibiting high salad-oil splitting activity was obtained in Example 29. Further, in the case of this Example 29, a transparent conductive film was provided as a pre-coat. Thus, the intensity of electromagnet waves having come from the illuminating lamp (namely, a fluorescent lamp) was reduced. Further, there was only a very small quantity of dust adhered thereto due to static electricity.

Example 30

This Example 30 was obtained by forming a titanium dioxide film on the surface of the glass container of a halogen lamp. In this case, a halogen lamp JD100V/250W (manufactured by Toshiba Lighting Technology Corporation (incidentally, "JD100V/250W" was a trade name used by Toshiba Lighting Technology Corporation)).

Thickness of the titanium dioxide film was set at 4.2 $\mu$m. The structure and manufacturing method of the titanium dioxide film were the same as employed in the aforementioned Example 28. Therefore, the detailed description of this titanium dioxide film is omitted herein.

Further, the thickness of the film of this Example 30, and results of the measurement of the salad oil splitting activities, and the illuminance of the visible light having wavelengths in a range, whose center wavelength was 550 nm, and the intensity (or power density) of the ultraviolet light having wavelengths in a range, whose center wavelength was 365 nm, are listed in the table of FIG. 7.

As is apparent from the table of FIG. 7, the salad-oil splitting activity of this Example 30 is high, namely, 10.8 per day·cm$^2$. Moreover, The intensity of ultraviolet light of this Example 30 is 9.6% (namely, the decreasing ratio is 90.4% ) of a halogen lamp (namely, Comparative Example 8 (to be described later)) having the same configuration except that no titanium dioxide was formed. Thus, this Example 30 has excellent fat-and-oil splitting activity and moreover, can extremely effectively cut off the ultraviolet light.

Example31 and Example 32

These Examples have the same configuration as Example 30 does, except that the film thickness was changed. Further, the thickness of the film, and results of the measurement of the salad oil splitting activities, and the illuminance of the visible light having wavelengths in a range, whose center wavelength was 550 nm, and the intensity (or power density) of the ultraviolet light having wavelengths in a range, whose center wavelength was 365 nm, are listed in the table of FIG. 7, correspondingly to each of these Examples 31 and 32. Thus, the detailed description of the configuration of each of these Examples 31 and 32 is omitted herein.

Example 33 and Example 34

These Examples 33 and 34 were obtained by providing a precoat layer, which was made of SiO$_2$, between the glass container of a halogen lamp and the titanium dioxide film thereof. Further, these Examples have the same configuration as the aforementioned Examiner 30 does, except that the thickness of the precoat layer and the titanium dioxide film. Moreover, these Examples 33 and 34 were manufactured by the similar method as used for manufacturing the Example 30. Thus, the thickness of the film, and results of the measurement of the salad oil splitting activities, and the illuminance of the visible light having wavelengths in a range, whose center wavelength was 550 nm, and the intensity (or power density) of the ultraviolet light having wavelengths in a range, whose center wavelength was 365 nm, are listed in the table of FIG. 9, correspondingly to each of these Example 33 and Example 34. Therefore, the detailed description of the configuration and manufacturing method of these Examples is omitted herein. Although the glass container of the halogen lamp is usually made of quartz glass, it was noticed that the provision of the precoat layer made of SiO$_2$ resulted in the improvement of the adhesion between the titanium dioxide film and the glass container and the increase in the visible light transmittance.

The salad-oil splitting activity is high, namely, 1.7 to 11.0 $\mu$g per day·cm$^2$. Further, the intensity of the ultraviolet light having wavelengths in a range, whose center wavelength was 365 nm is 7 to 19% (namely, the decreasing ratio of 81 to 93% ) of that of the halogen lamp (namely, Comparative Example 8) having the same configuration except that no titanium dioxide film was formed. Thus, it can be verified that these Examples have excellent fat-and-oil splitting activity and can cut off the ultraviolet light extremely effectively.

Example 35

This Example 35 was obtained by forming a titanium dioxide film on the surface of a glass container for an ultraviolet light lamp. Incidentally, in this case, a black-light fluorescent lamp FL10BLB manufactured by Toshiba lighting Technology Corporation (additionally, "FL 10BLB" is a trade name used by Toshiba lighting Technology Corporation).

Thickness of the titanium film was set at a value of 0.8 $\mu$m. The detailed description of the configuration and manufacturing method of this titanium dioxide film is omitted herein.

The illuminance of the visible light having wavelengths in a range, whose center wavelength was 550 nm, and the intensity (or power density) of the ultraviolet light having wavelengths in a range, whose center wavelength was 365 nm, are listed in the table of FIG. 9, correspondingly to each of this Example. As shown in the table of FIG. 9, the salad-oil splitting activity of this Example 35 is extremely high, namely, 8.7 $\mu$g/Hr·cm$^2$. However, the intensity of the ultraviolet light having wavelengths in a range, whose center wavelength was 365 nm is 35% (namely, the decreasing ratio of 65%) of that of the ultraviolet lamp (namely, a black light in the case of Comparative Example 9) having the same configuration except that no titanium dioxide film was formed therein. Thus, it is understood that this Example can radiate ultraviolet light having sufficient intensity.

Examples 36 to 39

Each of these Examples was obtained by providing a precoat layer, which is made of SiO$_2$, between the glass container of the ultraviolet lamp (namely, a black light) and the titanium oxide film of this Example 35. Moreover, the configuration and manufacturing method of each of these Example 36 to Example 39 was similar to those of the Example 35 except that the precoat layer was provided therein and that the thickness of the titanium dioxide film was changed. Incidentally, the precoat layer was the same as of the Example 25. Thus, the thickness of the precoat layer, the thickness of the film, and results of the measurement of the salad oil splitting activities, and the intensity (or power density) of the ultraviolet light having wavelengths in a range, whose center wavelength was 365 nm, are listed in the table of FIG. 9, correspondingly to each of these Example 33 and Example 34. As is apparent from the table of FIG. 9, the salad-oil splitting activities of these Example 36 to Example 39 are extremely high, namely, 5.4 to 12.2 $\mu$g/Hr·cm$^2$. However, the intensity of the ultraviolet light having wavelengths in a range, whose center wavelength in the case of the Example 36 to Example 39 was 365 nm is 22 to 48% (namely, the decreasing ratio of 52 to 78%) of that of the ultraviolet lamp (namely, a black light in the case of Comparative Example 9) having the same configuration except that no titanium dioxide film was formed therein. Thus, it is understood that these Example can radiate ultraviolet light having sufficient intensity.

Comparative Example 4

This Comparative Example had the same configuration as Example 21 does, except that the film thickness was thin, namely, 0.05 $\mu$m. Further, this Comparative Example was produced by the same method as used for producing Example 21. Moreover, the film thickness of this Comparative Example and the illuminance of the visible light and the fat-and-oil splitting activity of the photocatalyst are listed in the table of FIG. 9, correspondingly to this Comparative Example. Thus, the detailed description of the configuration and manufacturing method of this Comparative Example is omitted herein. As is understood from the table of FIG. 9, this Comparative Example exhibited good visible light illuminance but almost no photocatalytic activity.

Comparative Example 5

This Comparative Example had the same configuration as Example 21 does, except that the temperature when forming the film was 380 degrees centigrade. Further, this Comparative Example was produced by the same method as used for producing Example 21. Moreover, the film thickness of this Comparative Example and the illuminance of the visible light and the fat-and-oil splitting activity of the photocatalyst are listed in the table of FIG. 9, correspondingly to this Comparative Example. Thus, the detailed description of the configuration and manufacturing method of this Comparative Example is omitted herein. Incidentally, in the case of this Comparative Example, it was confirmed that the titanium dioxide film 12 does not contain anatase crystals at all. Moreover, there was residual carbon which would be originated from the incomplete combustion of organic substances. It is conjectured that this resulted in low light transmittance and in very low photocatalytic activity.

Comparative Example 6

This Comparative Example was obtained by setting the film thickness of the precoat layer, which was made of SiO$_2$ and was formed between the titanium dioxide film 12 and the glass container 11 of the Example 25, at 0.01 $\mu$m and by then forming a titanium dioxide film 12, which was 0.1 $\mu$m in thickness, on this precoat layer through the same method as utilized in the case of the Example 25. Moreover, the film thickness of this Comparative Example and the illuminance of the visible light and the fat-and-oil splitting activity of the photocatalyst are listed in the table of FIG. 9, correspondingly to this Comparative Example. Thus, the detailed description of the configuration and manufacturing method of this Comparative Example is omitted herein. Incidentally, in the case of this Comparative Example, it is conjectured that the low photocatalytic activity of this Comparative Example would be the fact that the thickness of each of the precoat layer and the titanium dioxide film was very small.

Comparative Example 7

This Comparative Example was an illuminating lamp (namely, a fluorescent lamp) which had the same configuration as Example 21 did, except that no titanium dioxide film was provided therein. Further, the illuminance of the visible light and the intensity (or power density) of the ultraviolet light having wavelengths in a range, whose center wavelength was 365 nm, and results of the measurement of the salad oil splitting activities, and are listed in the table of FIG. 9. correspondingly to this Comparative Example 7.

Comparative Example 8

This Comparative Example was an illuminating lamp (namely, a 250-W halogen lamp) which had the same configuration as Example 30 did, except that no titanium dioxide film was provided therein. Further, the illuminance of the visible light and the intensity (or power density) of the ultraviolet light having wavelengths in a range, whose center wavelength was 365 nm, and results of the measurement of the salad oil splitting activities, and are listed in the table of FIG. 9. correspondingly to this Comparative Example 8.

Comparative Example 9

This Comparative Example was an illuminating lamp (namely, a 10-W black light) which had the same configuration as Example 35 did, except that no titanium dioxide film was provided therein. Further, the illuminance of the visible light and the intensity (or power density) of the ultraviolet light having wavelengths in a range, whose center wavelength was 365 nm, and results of the measurement of the salad oil splitting activities, and are listed in the table of FIG. 9. correspondingly to this Comparative Example 9.

Incidentally, there is no particular restraint on the glass container of the present invention, as long as the glass container is used for a fluorescent lamp, a halogen lamp tube or a black light tube.

Further, in the case that the glass container is made of soda lime glass or the like, the fat-and-oil splitting activity of the titanium dioxide film is hindered by alkaline ingredients, such as sodium, diffused from the glass of the glass container. It is, therefore, desirable for preventing the diffusion of such an ingredient to provide a precoat layer on the surface of the glass container. In this case, even glass, such as inexpensive soda lime glass, from which an alkaline ingredient may be diffused, can be used advantageously.

Furthermore, if the thickness of the titanium dioxide film is less than 0.1 μm, the activity is low. Thus, although the film exhibits the light transparency to some extent, the practicality of such a lamp is low or poor. Conversely, if exceeding 5 μm, the lamp has advantages in that the activity can be maintained at a high level and that the coloring due to the interference of light is suppressed. However, there may easily occur the following defects that the film becomes liable to be clouded, that the flaking of the film may occur, and that the deposition (or film formation) time is lengthened.

Moreover, even in the case where the titanium dioxide is provided on the soda lime glass or the like, the photocatalytic activity can be secured in the vicinity of the surface of the titanium dioxide film by setting the film thickness at a relatively large value, for example, 0.3 to 5 μm, and further setting the concentration of sodium contained in the titanium dioxide film in such a manner as to decrease in a direction from a glass-container side to the surface of the film. In this case, the precoat layer can be omitted If the film thickness of the precoat layer is set in such a way as to be less than 0.02 μm, the ability to prevent the diffusion of an alkaline ingredient is degraded. Conversely, if the film thickness of the precoat layer is set in such a way as to be less than 1 μm, the light transmittance is lowered and the deposition (or film formation) conditions are complicated without a hindrance to the ability to prevent the diffusion of the alkaline ingredient. Thus, this case is not preferable. Therefore, the diffusion of the alkaline ingredient, such as sodium, from the glass container can be prevented by providing the precoat layer. Consequently, the film thickness of the titanium dioxide film itself can be reduced to a very small value, and a titanium dioxide film having high light-transmittance in the visible light region can be formed.

Example 40

This example was an illuminating device for use in a tunnel, which is configured by using a photocatalyst structure of the present invention.

Figure 12:
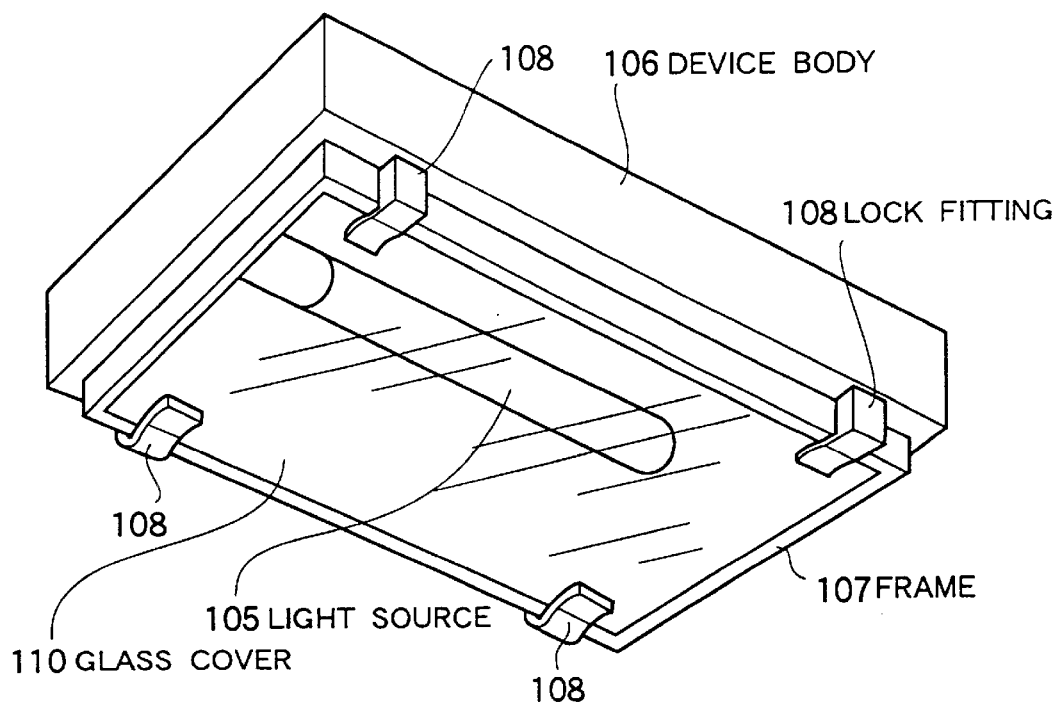
FIG. 12 is a perspective external view of an illuminating device for use in a tunnel, which is Example 41 according to the present invention.

FIG. 12 is an external perspective view of the illuminating device for use in a tunnel, which is Example 40. As shown in this figure, in the case of this illuminating device for use in a tunnel, a light source 105 was provided and accommodated in a device body 106 of the device. Further, the device body 106 was opened at a side (namely, a downward side) thereof and was shaped like a box (namely, a rectangular prism). Moreover, a frame 107 was attached to the edge portions of this opened side face. The glass cover 110 was fitted into this frame 107. This glass cover 110 was detachably attached to the frame 107 by lock fittings 108.

Figure 13:
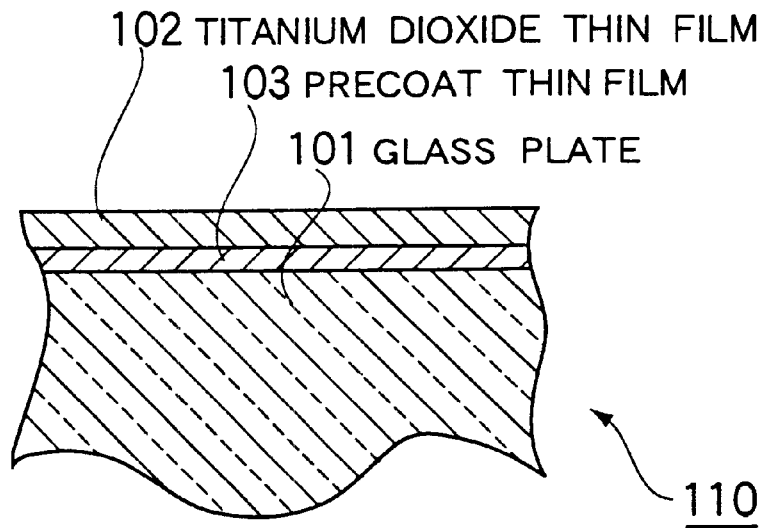
FIG. 13 is a partially sectional view of a cover glass of the device shown in FIG. 12.

FIG. 13 is a partially sectional view of the glass cover 110. As shown in this figure, this glass cover 110 was obtained by a precoat film 103, which was constituted by a silica film having a thickness of 0.1 μm, and a titanium dioxide film 102, which was 0.16 μm in thickness, on a surface (namely, an outward face) of the glass plate 101 which was 5 mm in thickness.

This glass cover 110 was manufactured as follows. Namely, first, an end portion, which is 2 cm in length, of a short side of a glass plate, which was 66 cm in longitudinal length and 33 cm in lateral length and 5 mm in thickness, and the entire surface of one of side faces of this glass plate were masked with paper tape. Then, 5L (litters) of a dipping chemical "ATOLON Nti-500" manufactured by Nippon Soda Co., Ltd. (incidentally, "ATOLON Nti-500" is a trade name) 5L was put into a dipping tank constituted by a box-type tank made of polypropylene, which was 70 cm in depth and 40 cm in width and 2 cm in length. The glass plate was suspended by fastening the top end portion of the aforementioned glass plate, which was masked with the paper tape, with a clip. Then, the glass plate was dipped into the dipping tank slowly at a speed of 20 cm/min. After the still standing of the glass late for 5 minutes, the glass plate was pulled up slowly. Thereafter, the glass plate was caused to remain being in such a state for 5 minutes. Subsequently, the masking tape was peeled off and the glass plate was put into an electric furnace heated to 500 degrees centigrade, by being suspended. Thus, the heat treatment was performed on the glass plate. Then, the glass plate was put into a preliminary furnace heated to 200 degrees centigrade and was air-cooled for 20 minutes. Subsequently, the glass plate was taken out therefrom and was cooled. Thereafter, a silica precoat film 103 was on one of the side faces of the glass plate. As a result of measurement of the film thickness by using a reflection interference method, it was verified that a silica film having a film thickness of 0.1 μm was obtained. Next, masking tape was stuck to the entire surface of the other side face, on which no silica film was deposited, of the glass plate. Then, 5 L of a dipping chemical "NTi-092", which was manufactured by Nippon Soda Co., Ltd. ("NTi-092" is a trade name)), was put into a dipping tank of the same type. Then, a deposition (or film formation) process was performed twice by utilizing the same method as used for depositing the silica film on the glass plate, under the heat treatment conditions. Thus, a glass cover 110 was manufactured by depositing a titanium dioxide thin plate 102 on one of the side faces of a glass plate. Similarly, as a consequence of measurement of the film thickness by using the reflection interference method, it was found that the thickness of the titanium dioxide film 102 was 0.08 μm.

This illuminating device for use in a tunnel was installed at a side of a trunk road, the traffic of trucks exhausting a diesel exhaust gas on which was 1000 per day. The conditions of stains left on this device was compared with those of stains left on another illuminating device that uses a cover glass on the surface of which no titanium dioxide film (namely, a photocatalyst) was formed. Namely, the degree of the stain was measured by means of a spectrophotometer by removing the glass covers at an initial time, and one month later and three months later by measuring the linear transmittance corresponding to light having a wavelength of 550 nm. In the case of this Example 40, the linear transmittance was 84% at the initial time, 83% at the time when one month has passed since the initial time, and 81% at the time when three months have passed since the initial time. There was caused almost no variation in the linear transmittance. In contrast, in the case of the illuminating device using the cover glass provided with no titanium dioxide film, the linear transmittance was 88% at the initial time, but was 74% at the time when one month has passed since the initial time, and 56% (namely, the linear transmittance was lowered by about 30% ) at the time when three months have passed since the initial time.

Example 41

FIG. 14 was a sectional view of a window glass which is Example 14 of the present invention. Hereinafter, the window glass will be described hereinbelow by referring to FIG. 14.

In the case of the window glass of FIG. 14, a soda lime glass (plate) was used as a glass plate 21 acting as a substrate. Namely, a titanium dioxide film 2 is a titanium dioxide film which contains anatase crystals and is 4.7 μm in thickness.

This was produced by performing the following process.

First, a soda lime glass 21 whose width, length and thickness were 15 cm, 20 cm and 1 mm, respectively, was set in a pyro-sol film forming device. Moreover, a raw material solution obtained by dissolving 0.5 mol of titanium tetraisoproxide in 1L of acetylacetones was atomized by ultrasonic waves and was then introduced into the aforementioned film forming device, wherein a film forming operation was performed at 500 degrees centigrade for about 80 minutes. Thus, a titanium dioxide film was formed on the glass container 11 for the fluorescent lamp. Incidentally, according to a result of analysis of this titanium dioxide film 2 based on X-ray diffraction performed by cutting a part of this glass plate, it was verified that this film 22 contained anatase crystals.

Next, the photocatalytic activity, which acts as an indication of the anti-fouling function of the obtained glass plate coated with the titanium dioxide photocatalyst film, and the linear (light) transmittance thereof, which acts as an indication of the transparency, were measured by performing the following method.

Method for Measuring Anti-fouling Function

Experiment on the decomposition of salad oil, which was put on the market and contained linoleic acid as a major ingredient, was performed. Namely, first, 0.1 to 0.15 mg of salad oil was applied onto an area of 1 cm$^2$ of the surface of the glass plate by using paper. The amount of the applied salad oil was obtained by measuring the weight of the plate before and after the application of the salad oil. Further, such a glass plate was set so that the intensity (or power density) of ultraviolet light, which includes at least a part of light whose wavelength ranges 300 to 400 nm, on the surface of the glass plate was 5 mW/cm$^2$. Then, the light was irradiated on the glass plate. Thereafter, the weight of the glass plate was measured at predetermined moments by means of a precision balance so as to find the relation between the elapse of time and a reduction in the weight of the glass plate. This relation is employed as an indication (or indicator) representing the splitting activity.

Method for Measuring Linear Light Transmittance

Test piece, which was 10 mm in width and 20 mm in length, was prepared by cutting a part of the glass plate provided with a titanium dioxide film. Similar test piece was prepared by using another glass plate which was not provided with a titanium dioxide film. Moreover, one of these test pieces was used as a specimen, and the other was used as a reference. Thus, the linear transmittance corresponding to each of the wavelengths of 550 nm and 365 nm of the light was measured by a spectrophotometer UV-3100 manufactured by Shimadzu Corporation (incidentally, "UV-3100" is a trade name).

Results of the measurement by using the aforementioned methods were as follows: the salad-oil splitting activity was 12.5 μg/Hr ·cm$^2$; the linear transmittance corresponding to the light having the wavelength of 550 nm was 75%; and the linear transmittance corresponding to the light having the wavelength of 365 nm was 10%. Consequently, it was verified that this Example has the excellent fat-and-oil splitting activity and the sufficient transparency.

Furthermore, the salad oil splitting activity was similarly studied by adjusting the black light so that the intensity (or power density) of 5 mW/cm$^2$ was obtained on the surface of the titanium dioxide film by irradiating the film with light from a black light FL10BLB manufactured by Toshiba Lighting Technology Corporation (incidentally, "FL10BLB" is a trade name). As a result, it was verified that a value 11.7 μg/Hr·cm$^2$, which was almost equal to the value measured in the herein-above mentioned case, of the fat-and-oil splitting activity was obtained. This reveals that, in the case where a titanium dioxide photocatalyst was applied onto one of the side faces of the glass plate, not only light sent from the surface thereof, onto which the titanium dioxide film was applied, but also light sent from the other side face thereof can be utilized.

Example 42 to Example 44

These Examples have similar configurations as Example 41 does, except that the film thickness of the titanium dioxide film was changed. Further, these Examples were manufactured by the manufacturing method to that used in the case of Example 41. Moreover, the thickness of the film, and results of the measurement of the salad oil splitting activities, and the linear transmittance are listed in the table of FIG. 15, correspondingly to each of these Examples 42 to Example 44. Thus, the detailed description of the configuration of each of these Examples 42 to Example 44 is omitted herein.

As described in the table of FIG. 15, each of these Examples has the excellent fat-and-oil splitting activity and the sufficient transparency.

Example45 to Example 47

Figure 16:
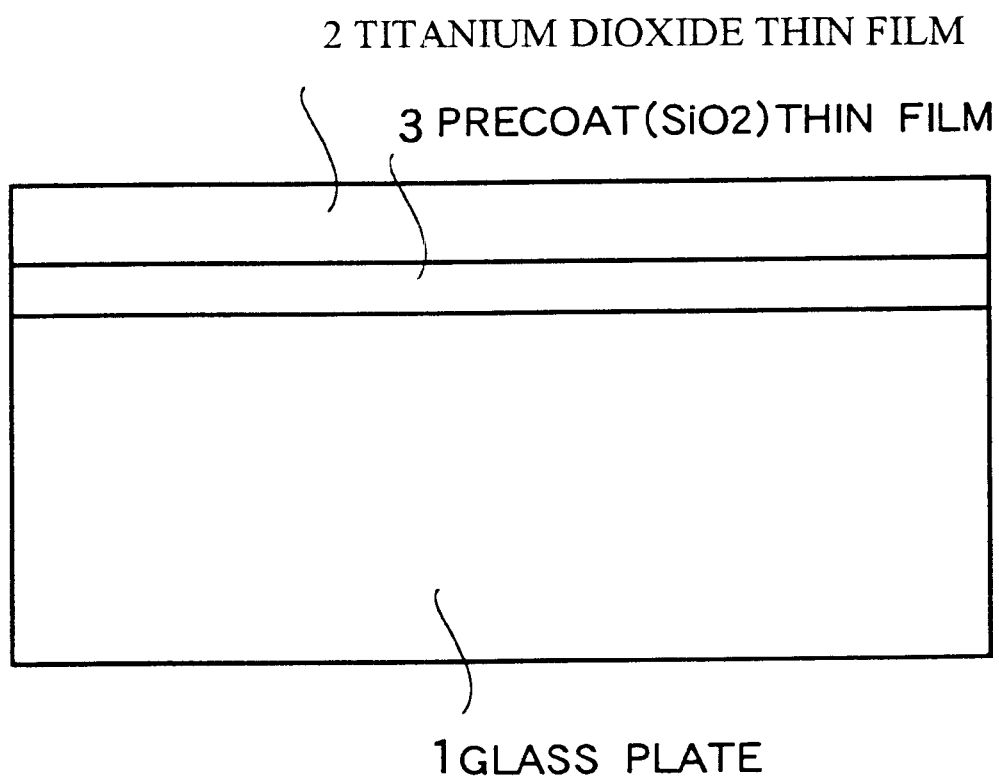
FIG. 16 is a sectional view of a window glass of Example 46 according to the present invention.

These Examples have similar configurations as Example 41 does, except that the precoat film constituted by $SiO_2$ was formed between the titanium dioxide film 32 and the glass plate 21 of Example 41 by the dip-coating, as shown in FIG. 16. Further, these Examples were manufactured by the manufacturing method similar to that used in the case of Example 41. Moreover, the thickness of the film, and results of the measurement of the salad oil splitting activities, and the linear transmittance are listed in the table of FIG. 15, correspondingly to each of these Examples 45 to Example 47. Thus, the detailed description of the configuration of each of these Examples 45 to Example 47 is omitted herein.

As described in the table of FIG. 15, in comparison with Example 41 to Example 44, which are not provided with a precoat, each of these Examples exhibits the excellent fat-and-oil splitting activity, even when the thickness of the titanium dioxide film is reduced. and the sufficient transparency. Therefore, it is understood that higher transparency can be secured.

Example 48

This Example was obtained by adding silver to the titanium dioxide film 22 of Example 47. Glass plate, onto which the titanium dioxide film was deposited until the film thickness reaches 3.0 μm similarly as in the case of Example 47, was put into a glass container which was 10 cm in width, 15 cm in length and 1 cm in depth. Then, 30 ml of a 1 percent silver nitrate solution was added thereto. Subsequently, light was irradiated thereto from a 400-W high-voltage mercury lamp for 40 minutes. Thus, a minute quantity of metallic silver was deposited on the titanium dioxide film by photoreduction. Amount of deposited silver was obtained by SEM-EDS method. Results of measurement of the salad oil splitting activity and the linear transmittance are presented in tabular form in FIG. 15.

Example 49

This Example 49 was obtained by performing a method similar to the method used in the case of Example 25 to Example 27 as follows. Namely, a precoat film constituted by a SiO2 film was formed between the titanium dioxide film 22 and the glass plate 21 through a dipcoating process. Subsequently, a precoat (thin) film constituted by an indium tin oxide (ITO) film including tin oxide by 8% was formed by a pyro-sol device so that the thickness of this (thin) film was 0.2 $\mu$m. Thereafter, the titanium dioxide (thin) film was provided by performing the similar method as performed in the case of Example 41. Incidentally, results of the measurement of the film thickness of each of the precoat films, the salad oil splitting activities, and the linear light transmittance are listed in the table of FIG. 15. Further, the detailed description thereof is omitted herein.

As is seen from the table of FIG. 15, in comparison with the case of the titanium dioxide films of Example 45 to Example 47 which had no precoat layers, a thinner film exhibiting high salad-oil splitting activity was obtained in Example 49. Further, in the case of this Example 49, a transparent conductive film was provided as a pre-coat. Thus, the intensity of electromagnet waves having come from the illuminating lamp (namely, a fluorescent lamp) was reduced. Further, there was only a small quantity of dust adhered thereto due to static electricity.

Comparative Example 10

This Comparative Example had the same configuration as Example 41 does, except that the film thickness was thin, namely, 0.05 $\mu$m. Further, this Comparative Example was produced by the same method as used for producing Example 41. Moreover, the film thickness of this Comparative Example, results of measurement of the fat-and-oil splitting activity of the photocatalyst and the linear light transmittance are listed in the table of FIG. 15, correspondingly to this Comparative Example. Thus, the detailed description of the configuration and manufacturing method of this Comparative Example is omitted herein.

As is shown in the table of FIG. 15, this Comparative Example exhibited good transparency but almost no photocatalytic activity.

Comparative Example 11

This Comparative Example has a structure, which is similar to the structure of Example 41 except that the temperature at the time of forming the titanium dioxide film was changed into 360 degrees centigrade, and was produced by a producing method similar to that employed in the case of Example 41. Thus, the film thickness of this Comparative Example, results of measurement of the fat-and-oil splitting activity of the photocatalyst and the linear light transmittance are listed in the table of FIG. 15, correspondingly to this Comparative Example. Further, the detailed description thereof is omitted. Incidentally, in the case of the glass plate provided with the titanium dioxide film, according to a result of analysis of the titanium dioxide film 2, which was produced in this way, based on X-ray diffraction, it was verified that this film 22 did not contained anatase crystals at all.

Incidentally, there is no particular restraint on the composition of the window glass of the present invention, as long as the window glass of the present invention is used for windows of ordinary buildings, and windows of transportation vehicle such as an automobile and a train.

Further, in the case that the glass plate acting as the substrate is made of soda lime glass or the like, the fat-and-oil splitting activity of the titanium dioxide film is hindered by alkaline ingredients, such as sodium, diffused from the substrate. It is, therefore, desirable for preventing the diffusion of such an ingredient to provide a precoat film on the surface of the substrate. In this case, even glass, such as inexpensive soda lime glass, from which an alkaline ingredient may be diffused, can be used advantageously.

Furthermore, the thickness of the titanium dioxide film usually ranges from 0.1 to 5 $\mu$m. If the thickness of the titanium dioxide film is less than 0.1 $\mu$m, the film exhibits the sufficient light transparency but the activity is low. Thus, the practicality of such window glass is low or poor. Conversely, if exceeding 5 $\mu$m, the lamp has advantages in that the activity can be maintained at a high level and that the coloring due to the interference of light is suppressed. However, there may easily occur the following defects that the film becomes liable to be clouded, that the flaking of the film may occur, and that the deposition (or film formation) time is lengthened.

Moreover, titanium dioxide can be utilized as a photocatalyst in the vicinity of the surface of the titanium dioxide film by setting the film thickness of the film, which is to be formed, at a relatively large value, for example, 0.3 to 5 $\mu$m, and further setting the concentration of sodium contained in the titanium dioxide film in such a manner as to decrease gradiently or inclinedly with respect to a certain direction. In this case, the precoat film can be omitted.

Thickness of the precoat layer is usually within a range of 0.02 to 1 $\mu$m. If the film thickness of the precoat layer is set in such a way as to be less than 0.02 $\mu$m, the ability to prevent the diffusion of an alkaline ingredient is degraded. Conversely, if the film thickness of the precoat layer is set in such a way as to be less than 1 $\mu$m, the light transmittance is lowered and the deposition (or film formation) conditions are complicated without a hindrance to the ability to prevent the diffusion of the alkaline ingredient. Thus, this case is not preferable. Therefore, the diffusion of the alkaline ingredient, such as sodium, from the substrate can be prevented by providing the precoat layer. Consequently, the film thickness of the titanium dioxide film itself can be reduced to a very small value, and a titanium dioxide film having high light-transmittance in the visible light region can be formed.

Incidentally, there is no particular restraint on the material of the transparent substrate used in the photocatalyst structure of the present invention, as long as the transparent substrate has optically predetermined transparency. To adduce actual examples, pyrex glass, quartz glass, lead glass and soda lime glass and so forth may be employed. Practically, inexpensive soda lime glass is mainly used. Further, quartz glass, which contains no alkaline ingredients such as sodium, and borosilicate glass, which contains little alkaline ingredients such as sodium, may be preferably used in the glass substrate. In the case where the transparent substrate is made of soda lime glass, the photocatalytic action of the titanium dioxide film is hindered by alkaline ingredients such as sodium, which are diffused from the substrate. It is, therefore, preferable for preventing the diffusion to provide a precoat film on the transparent substrate. In this may easily case, the photocatalyst structure can be advantageously used even when the transparent substrate, in which alkaline ingredients such as inexpensive soda lime glass, may be diffused.

The titanium dioxide film has a thickness of 0.1 to 5 μm. If not more than 0.1 μm, the film exhibits the transparency but has low photocatalytic activity. Thus, the photocatalyst structure loses the practicality. In contrast, if the thickness of the titanium dioxide film exceeds 5 μm, the photocatalyst structure has advantages in that high photocatalytic activity can be maintained and that the risk of coloration due to optical interference can be reduced. The photocatalyst structure, however, tends to have defects in that the film becomes clouded and inclined and that it takes much time to peel and form a film.

Further, it is possible to utilize a titanium dioxide, which is provided in the vicinity of the surface of the film, as a photocatalyst structure by setting the thickness of the titanium dioxide film, which should be formed, at a large value, for example, 0.3 to 5.0 μm and by setting the concentration of sodium, which is contained in the titanium dioxide film, in such a manner as to change decreasingly in the direction of thickness. In this case, the precoat film can be omitted.

The precoat film has a thickness of 0.02 to 0.2 μm. If the thickness thereof is not more than 0.02 μm, the ability to prevent the diffusion of alkaline ingredients is reduced. In contrast, if the thickness thereof is not less than 0.2 μm, there is no hindrance to the ability to prevent the diffusion of alkaline ingredients. However, the light transmissivity is reduced and an operation of forming a film becomes complex. Because the diffusion of alkaline ingredients such as sodium from the substrate is prevented by the precoat film, the thickness of the titanium dioxide film can be reduced. Moreover, the titanium dioxide film, whose transparency is higher in the visible range, can be formed.

As long as the light transmittance in the visible range is high and the diffusion of sodium from the substrate can be prevented, there is no restrain on the composition of a precoat film. For instance, a silicone dioxide film, a tin oxide film, an indium-doped tin oxide film, an indium oxide film, a tin-doped indium oxide film, a germanium oxide film, an aluminum oxide film, zirconium oxide film and a $SiO_2$+ $MO_X$ film (incidentally, $MO_X$ represents a kind of metallic oxide selected from the group of $P_2O_5$, $B_2O_3$, $ZrO_2$, $TiO_2$ and $Ta_2O_5$) can be cited as examples of the precoat film. From the view of the ability to prevent the diffusion of alkaline ingredients, a silicone dioxide film or a film, in which 5% by weight of $P_2O_5$ is added to $SiO_2$, is particularly preferable.

Moreover, the condition necessary to obtain a titanium dioxide film, which has a high photocatalytic activity, is that this film contains anatase crystals. When the temperature, at which the film is formed or at which the heat treatment is performed after forming the film, is high, the anatase crystals causes phase transition. As a result, a part of the anatase crystals are changed into rutile crystals. Therefore, an anatase-type titanium dioxide film containing rutile crystals is preferably used. It is, however, undesired that all of the anatase crystals are changed into rutile crystals at a high temperature. This is because of the fact that in such a case, owing to the phase transition, the titanium dioxide becomes clouded and thus the light transmittance in the visible range is decreased.

In the case of the photocatalyst structure of the present invention, although the pyro-sol method is the most suitable for forming a film, commonly known methods for forming films can be employed for forming both of the precoat film and the titanium dioxide film. Namely, a sputtering method, an electron beam evaporation method, an ion plating method, a chemical vapor deposition (CVD) method, a spraying method, a dipping method and so forth may be applied to the photocatalyst structure of the present invention by devising a process for controlling the formation of a film. Incidentally, methods, such as the pyro-sol method and the spraying method, for spraying a mist at normal pressure are preferable, because the application of such methods to the case of actually and industrially manufacturing photocatalyst structures can be achieved by spraying a mist during a glass plate is still hot in the process of cooling the glass plate which is being produced. Additionally, film forming methods, in which a substrate should be maintained at a high temperature, which is not lower than the softening temperature of glass, for example, at a high temperature, which is not lower than 600 degrees centigrade, are not desirable because such methods cause the deformation of the substrate and accelerate the diffusion of alkaline ingredients.

What is called the pyro-sol method is desired as the method for forming films, for the following reasons. First, inexpensive titanium alkoxide of high purity is used as the material. Further, the films can be formed at a high speed. Moreover, a high-activity titanium dioxide film containing anatase crystals can be obtained in such a way as to be highly uniform and have a large area. Furthermore, the formation of the films can be achieved at a temperature which is not higher than the softening temperature of glass, namely, at a temperature which is 400 to 500 degrees centigrade or so. Such a temperature is an adequate temperature at which the diffusion of sodium can be retarded. Further, the diffusion thereof can be blocked by a precoat layer. The pyro-sol method is a kind of an atmospheric pressure chemical vapor cracking method (a CVD method) and is used to form the precoat film or the titanium dioxide by carrying out the process of performing the vapor-phase transport of a mist, which has undergone the ultrasonic atomization, to the substrate, which has been heated to 400 to 550 degrees centigrade, and further thermally decomposing the mist on the substrate.

Chemicals for producing precoat films are as follows. Namely, chemicals for producing $SiO_2$ are silicon alkoxides, such as $Si(OCH_3)_4$, $Si(OC_2H_5)_4$ and $SiCH_3(OCH_3)_4$, and condensation products thereof and silicon halide. Further, chemicals for producing tin oxide are $Sn(OCH_3)_4$, $Sn(OC_2H_5)_4$, $Sn(OC_4H_9)_4$, $Sn(AcAc)_4$, $Sn(OCOC_4H_{15})_4$, Sn $Cl_4$ and so on. Moreover, chemicals for producing indium oxide are $In(OCH_3)_3$, $In(OC_2H_5)_3$, In $Cl_3$, $In(AcAc)_3$, $In(NO)_3nH_{20}$ and so forth. Furthermore, chemicals for producing germanium oxide are $Ge(OC_2H_5)_4$, $Ge(OC_4H_9)_4$, $GeCl_4$ and so forth. Further, chemicals for producing aluminum oxide are $Al(OC_2H_5)_3$, $Al(iOC_3H_7)_3$, $Al(OC_4H_9)_3$, $Al(AcAc)_3$, $Al(NO_3)_{39}H_{20}$ and so on. Moreover, chemicals for producing phosphorus pentaoxide are $P(OC_2H_5)_3$, $PO(OCH_3)_3$, $PO(OC_2H_5)_3$, $H_3PO_4$, $P_2O_5$ and so forth. Additionally, chemicals for producing boron oxide are $B(OCH_3)_3$, $B(OC_2H_5)_3$, $B(OC_4H_9)_3$, $B(AcAc)_3$, $BC_{13}$, $H_3BO_3$ and so on. Among these, usually available chemicals are used. Incidentally, in the chemical formula, "AcAc" designates $C_5H_7O_2$ (namely, acetylacetonato).

Manufacturing chemicals for producing titanium dioxide films are as follows: titanium alkoxides such as $Ti(OC_2H_5)_4$, $Ti(iOC_3H_7)_4$, $Ti(OC_4H_9)_4$ and $Ti(OC_4H_9)_2C_{12}$; addition products and complexes obtained from titanium alkoxide and glycols such as ethylene glycol, or acids such as acetic acid and lactic acid, or alkanolamines such as triethanolamine, or -diketons such as acetylacetone; and chemicals obtained by dissolving chlorides such as $TiCl_4$ in alcohol for general application, such as ethanol, or in solvents such as acetic ester and diketone. In view of high activity and transmittance, -diketone complex solution obtained by dissolving titanium alkoxide in acetylacetone is particularly preferable.

Further, various known methods for accelerating a photocatalytic function can be employed appropriately. For example, a trace quantity of metal (for example, gold, platinum, palladium, silver, copper and so forth) may be carried by the titanium dioxide film.

Moreover, a conductive (thin) film (such as ITO film) may be formed on the precoat layer so as to impart an electromagnetic-wave shielding function thereto and thus impart conductiveness thereto. Furthermore, a titanium dioxide film may be formed thereon.

Additionally, especially, in the case that the precoat film (or layer) is composed of a plurality of layers, on one of which a conductive film is provided, so as to impart an electromagnetic wave shielding function thereto, a tin oxide film, an indium-doped tin oxide film, an indium oxide film a tin-doped indium oxide film are preferable. In especial, an indium oxide transparent film containing tin oxide by 5 to 10% is preferable because such an indium oxide transparent film has high visible light transmittance and excellent conductiveness.

As above described, the titanium dioxide photocatalyst structure can be used as a member of various structures especially required to have the transparency, for example, a glass window. The present invention can have distinguished advantages in that actions of eliminating carbon dioxide and air pollutants (for example, $NO_X$ and $SO_x$) from indoor space, of deodorizing the indoor space and of making the indoor space antibacterial, soil-resistant and mildew-proof are achieved by the window pane itself without using special equipment. Additionally, the present invention can obtain eminent merits in that in the case of cleaning the room by applying the photocatalyst structure to the window pane, sunlight can be extremely utilized. Moreover, especially, in the case of applying the photocatalyst structure of the present invention to a building or the like, in which glass materials are highly used, of the type that has become common in recent years, the photocatalyst structure of the present invention has immeasurable advantages in cleaning the living space. In addition, the photocatalyst structure of the present invention can be applied to a glass door or the like of a shelf, which includes the door or the like, for storing, for instance, precision devices such as a camera which should be kept away from molds and corrosion. Furthermore, the photocatalyst structure of the present invention can be used for various purposes which require transparent glass. For example, the photocatalyst structure of the present invention can be applied to glass covers for various electronic equipment and instrument, light fixtures such as a fluorescent lamp and a light bulb, a lens and a glass. Thus, the range of application of the photocatalyst structure of the present invention is extremely wide.

What is claimed is:

1. A titanium dioxide photocatalyst structure comprising:
   a transparent glass substrate having first and second opposing surfaces, said transparent glass substrate containing alkaline ingredients therein, the first surface of said substrate receiving light from an external light source;
   a titanium dioxide film having first and second opposing surfaces, a light transmittance of said titanium dioxide film being at least 50% for light having a wavelength of 550 nm, the first surface of said titanium dioxide film being formed on the second surface of said substrate, whereby light transmitted from said external source through the first and second opposing surfaces of said substrate and through the first surface of said titanium dioxide film to the second surface thereof causes photocatalytic activity to be generated on the second surface of said titanium dioxide film; and
   a transparent precoat film interposed between the second surface of said substrate and the first surface of said titanium dioxide film.

2. The titanium dioxide photocatalyst structure according to claim 1, wherein said transparent precoat film has a thickness of 0.02 $\mu$m to 0.2 $\mu$m.

3. The titanium dioxide photocatalyst structure according to claim 2, wherein said precoat film is composed of $SiO_2$.

4. A titanium dioxide photocatalyst structure comprising:
   a transparent substrate;
   a titanium dioxide film formed on said substrate, said titanium dioxide film having photocatalytic activity and a light transmittance of at least 50% for light having a wavelength of 550 nm; and
   a transparent precoat film disposed between the transparent substrate and the titanium dioxide film.

5. The titanium dioxide photocatalyst structure according to claim 4 wherein the precoat film has a thickness of 0.02 $\mu$m to 0.2 $\mu$m.

6. The titanium dioxide photocatalyst structure according to claim 4 wherein the precoat film is composed of $SiO_2$.

7. A method for producing a titanium dioxide photocatalyst structure according to claim 4 comprising a producing process which includes the step of forming the titanium dioxide film on the transparent substrate by a method selected from the group consisting of a pyro-sol method, a dipping method, a printing method and a CVD method.

8. A titanium dioxide photocatalyst structure comprising:
   a transparent substrate;
   a titanium dioxide film formed on said substrate, said titanium dioxide film having a thickness of 0.1 $\mu$m to 5 $\mu$m, photocatalytic activity and a light transmittance of at least 50% for light having a wavelength of 550 nm; and
   a transparent precoat film disposed between the transparent substrate and the titanium dioxide film.

9. The titanium dioxide photocatalyst structure according to claim 8 wherein the precoat film has a thickness of 0.02 $\mu$m to 0.2 $\mu$m.

10. The titanium dioxide photocatalyst structure according to claim 8 wherein the precoat film is composed of $SiO_2$.

11. A titanium dioxide photocatalyst structure comprising:
    a transparent substrate;
    a titanium dioxide film, containing an anatase crystal, formed on said substrate, said titanium dioxide film having photocatalytic activity and a light transmittance of at least 50% for light having a wavelength of 550 nm; and
    a transparent precoat film disposed between the transparent substrate and the titanium dioxide film.

12. The titanium dioxide photocatalyst structure according to claim 11 wherein the precoat film has a thickness of 0.02 $\mu$m to 0.2 $\mu$m.

13. The titanium dioxide photocatalyst structure according to claim 11 wherein the precoat film is composed of $SiO_2$.

* * * * *